(12) United States Patent
Nagai et al.

(10) Patent No.: US 10,107,338 B2
(45) Date of Patent: Oct. 23, 2018

(54) METHOD FOR MANUFACTURING OUTER JOINT MEMBER FOR CONSTANT VELOCITY UNIVERSAL JOINT AND OUTER JOINT MEMBER

(71) Applicant: NTN CORPORATION, Osaka (JP)

(72) Inventors: Hiromi Nagai, Shizuoka (JP); Naoki Nakagawa, Shizuoka (JP); Yasuhiko Sakakibara, Shizuoka (JP); Tatsuro Sugiyama, Shizuoka (JP); Masazumi Kobayashi, Shizuoka (JP)

(73) Assignee: NTN CORPORATION, Osaka (JP)

( * ) Notice: Subject to any disclaimer, the term of this patent is extended or adjusted under 35 U.S.C. 154(b) by 20 days.

(21) Appl. No.: 15/300,120

(22) PCT Filed: Mar. 20, 2015

(86) PCT No.: PCT/JP2015/058482
§ 371 (c)(1),
(2) Date: Sep. 28, 2016

(87) PCT Pub. No.: WO2015/146828
PCT Pub. Date: Oct. 1, 2015

(65) Prior Publication Data
US 2017/0074329 A1 Mar. 16, 2017

(30) Foreign Application Priority Data
Mar. 28, 2014 (JP) .................... 2014-068408

(51) Int. Cl.
*F16D 1/068* (2006.01)
*F16D 3/22* (2006.01)
(Continued)

(52) U.S. Cl.
CPC ................ *F16D 3/22* (2013.01); *B21K 1/765* (2013.01); *B23K 15/00* (2013.01);
(Continued)

(58) Field of Classification Search
CPC ......... Y10T 29/49533; Y10T 29/49535; Y10T 29/49536; Y10T 29/49686; Y10T 29/49696
See application file for complete search history.

(56) References Cited

U.S. PATENT DOCUMENTS

2010/0246326 A1   9/2010   Ichigo et al.
2014/0291301 A1*  10/2014  Tosaji ................. F16C 3/023
                                                 219/121.14
2014/0318250 A1   10/2014  Arai et al.

FOREIGN PATENT DOCUMENTS

JP    2009-103210    5/2009
JP    2010-230630    10/2010
(Continued)

OTHER PUBLICATIONS

English Translation Fuwa JP2013100859 (Pub date:May 23, 2013).*
(Continued)

*Primary Examiner* — Jason L Vaughan
*Assistant Examiner* — Amanda Meneghini
(74) *Attorney, Agent, or Firm* — Wenderoth, Lind & Ponack, L.L.P.

(57) ABSTRACT

Provided is a method of manufacturing an outer joint member of a constant velocity universal joint, which is constructed by welding a cup member and a shaft member, the method including: forming the cup member and the shaft member of medium carbon steel; preparing; preparing; bringing the joining end surface of the cup member and the joining end surface of the shaft member into abutment against each other; welding the cup member and the shaft member; and performing, after the welding, ultrasonic flaw detection-inspection from any one of a surface side of the cup member and a surface side of the shaft member, which
(Continued)

has the another one of the joining end surface of the cup member and the joining end surface of the shaft member.

9 Claims, 24 Drawing Sheets

(51) Int. Cl.
    *B23K 15/00*     (2006.01)
    *F16D 3/20*     (2006.01)
    *G01N 29/00*     (2006.01)
    *B23K 26/21*     (2014.01)
    *G01N 29/04*     (2006.01)
    *B21K 1/76*     (2006.01)
    *B23K 31/12*     (2006.01)
    *G01N 29/28*     (2006.01)

(52) U.S. Cl.
    CPC .......... *B23K 15/0046* (2013.01); *B23K 26/21* (2015.10); *B23K 31/125* (2013.01); *F16D 1/068* (2013.01); *F16D 3/20* (2013.01); *G01N 29/00* (2013.01); *G01N 29/043* (2013.01); *G01N 29/28* (2013.01); *F16D 2250/0076* (2013.01); *G01N 2291/0234* (2013.01); *G01N 2291/267* (2013.01); *G01N 2291/2626* (2013.01)

(56) References Cited

FOREIGN PATENT DOCUMENTS

| | | |
|---|---|---|
| JP | 2012-57696 | 3/2012 |
| JP | 2013-100859 | 5/2013 |
| WO | 2013/069433 | 5/2013 |
| WO | 2013/076850 | 5/2013 |

OTHER PUBLICATIONS

Chinese Office Action dated May 2, 2018 in corresponding Chinese Patent Application No. 201580011350.0 with English Translation of Search Report.
International Search Report (ISR) dated Jun. 23, 2015 in International (PCT) Application No. PCT/JP2015/058482.
International Preliminary Report on Patentability and Written Opinion of the International Searching Authority dated Oct. 4, 2016 in International (PCT) Application No. PCT/JP2015/058482.

\* cited by examiner

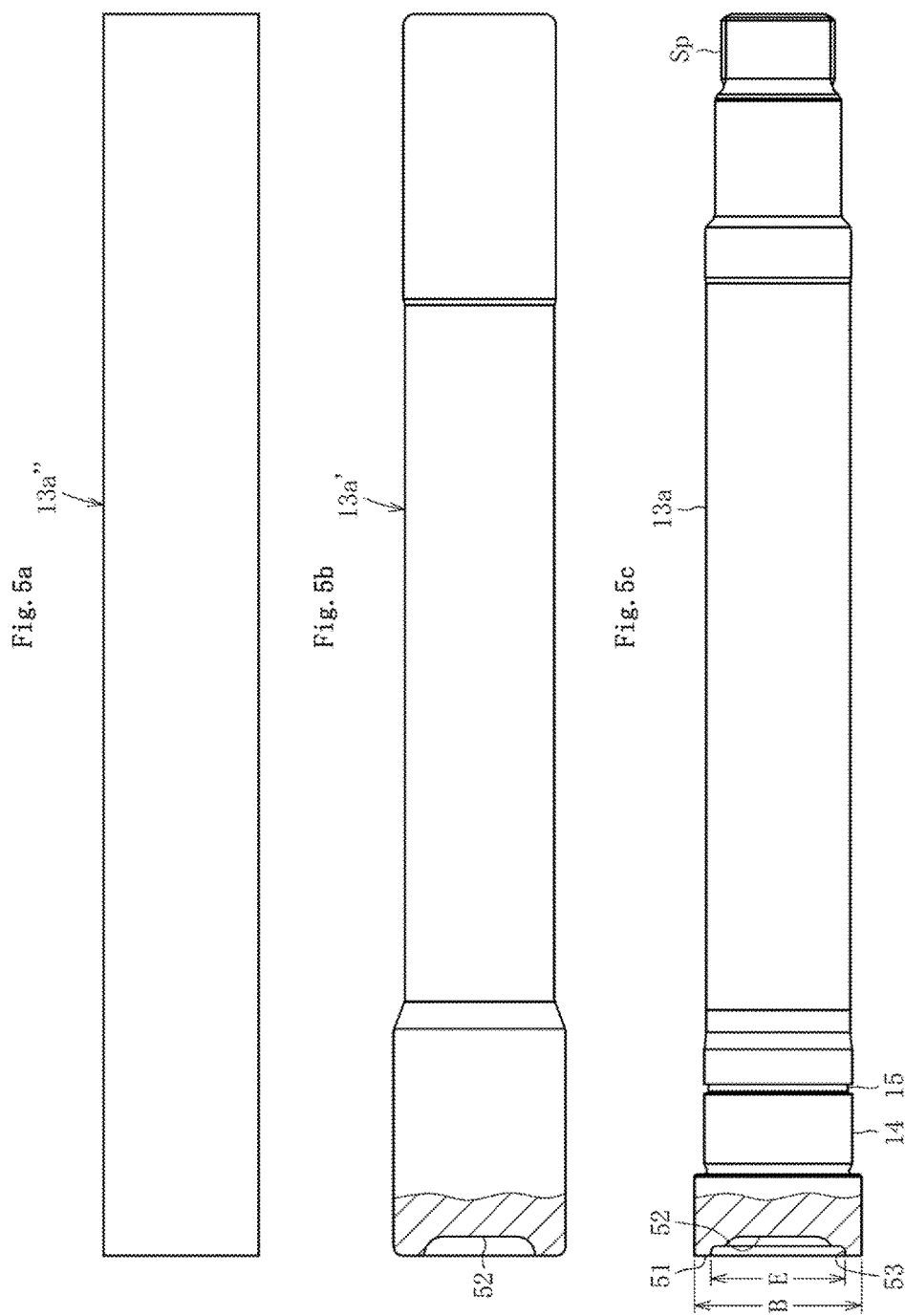

METHOD FOR MANUFACTURING OUTER JOINT MEMBER FOR CONSTANT VELOCITY UNIVERSAL JOINT AND OUTER JOINT MEMBER

TECHNICAL FIELD

The present invention relates to a method of manufacturing an outer joint member of a constant velocity universal joint and an outer joint member.

BACKGROUND ART

In a constant velocity universal joint, which is used to construct a power transmission system for automobiles and various industrial machines, two shafts on a driving side and a driven side are coupled to each other to allow torque transmission therebetween, and rotational torque can be transmitted at a constant velocity even when each of the two shafts forms an operating angle. The constant velocity universal joint is roughly classified into a fixed type constant velocity universal joint that allows only angular displacement, and a plunging type constant velocity universal joint that allows both the angular displacement and axial displacement. In a drive shaft configured to transmit power from an engine of an automobile to a driving wheel, for example, the plunging type constant velocity universal joint is used on a differential side (inboard side), and the fixed type constant velocity universal joint is used on a driving wheel side (outboard side).

Irrespective of the plunging type and the fixed type, the constant velocity universal joint includes, as a main component, an outer joint member including a cup section having track grooves formed in an inner peripheral surface thereof and engageable with torque transmitting elements, and a shaft section that extends from a bottom portion of the cup section in an axial direction. In many cases, the outer joint member is constructed by integrally forming the cup section and the shaft section by subjecting a rod-like solid blank (bar material) to plastic working such as forging and ironing or processing such as cutting work, heat treatment, and grinding.

Incidentally, as the outer joint member, an outer joint member including a long shaft section (long stem) may sometimes be used. In order to equalize lengths of a right part and a left part of an intermediate shaft, the long stem is used for an outer joint member on the inboard side that corresponds to one side of the drive shaft. The long stem is rotatably supported by a rolling bearing. Although varied depending on vehicle types, the length of the long stem section is approximately from 300 mm to 400 mm in general. In the outer joint member, the long shaft section causes difficulty in integrally forming the cup section and the shaft section with high accuracy. Therefore, there is known an outer joint member in which the cup section and the shaft section are formed as separate members, and both the members are joined through friction press-contact. Such a friction press-contact technology is described in, for example, Patent Document 1.

An overview of the friction press-contact technology for the outer joint member described in Patent Document 1 is described with reference to FIG. 23 and FIG. 24. An intermediate product 71' of an outer joint member 71 includes a cup member 72 and a shaft member 73, which are joined through the friction press-contact. As illustrated in FIG. 23, burrs 75 are generated in at least one of inner and outer diameters on a joining portion 74 along with the press-contact. In order to mount a rolling bearing (see FIG. 1) to a shaft section of the intermediate product 71' of the outer joint member 71, as illustrated in FIG. 24, it is necessary to remove the burrs 75 on the radially outer side of the joining portion 74 through processing such as turning. Although illustration is omitted, the intermediate product 71' is processed into a finished product of the outer joint member 71 through machining of a spline, snap ring grooves, and the like, and through heat treatment, grinding, and the like. Therefore, the outer joint member 71 and the intermediate product 71' have slight differences in shape, but illustration of the slight differences in shape is omitted in FIG. 24 to simplify the description, and the outer joint member 71 being the finished product and the intermediate product 71' are denoted by the reference symbols at the same parts. The same applies to the description below.

PRIOR ART DOCUMENTS

Patent Documents

Patent Document 1: JP 2012-57696 A

SUMMARY OF THE INVENTION

Problems to be Solved by the Invention

The burrs 75 on the joining portion 74 generated due to the friction press-contact described above are quenched by friction heat and cooling that follows the friction heat. Thus, the burrs 75 have a high hardness and a distorted shape extended in a radial direction and an axial direction. Therefore, as illustrated in FIG. 24, when removing the burrs 75 on the radially outer side through the turning, a tip for turning is liable to be significantly abraded due to the high hardness and cracked due to the distorted shape. Therefore, it is difficult to increase the turning speed. In addition, the cutting amount per pass of the tip for turning is decreased, and hence the number of passes is increased, which causes a problem in that the cycle time is increased to increase the manufacturing cost.

Further, in order to inspect a joining state of the joining portion 74 of the outer joint member 71, when ultrasonic flaw detection, which enables flaw detection at high speed, is to be performed, an ultrasonic wave is scattered due to the burrs 75 remaining on the radially inner side of the joining portion 74, and hence the joining state cannot be checked. Therefore, there occurs a problem in that total inspection through the ultrasonic flaw detection cannot be performed after the joining.

In view of the above-mentioned problems, when the components are joined through laser welding or electron beam welding, the surfaces of the joining portion may be prevented from being increased in thickness unlike the case of the friction press-contact. However, when the cup member 72 and the shaft member 73 as illustrated in FIG. 25 are brought into abutment against each other to be welded, a gas pressure in a hollow cavity portion 76 is increased due to processing heat during the welding, and after completion of the welding, the pressure is decreased. Due to the variation in the internal pressure of the hollow cavity portion 76, blowing of a molten material occurs. Thus, a recess is formed on radially outer surfaces of the welded portion, poor welding in terms of depth occurs, and air bubbles are generated inside the welded portion, thereby degrading the welding state. As a result, the strength of the welded portion is not stable, which adversely affects quality.

In addition, the cup member 72 and the shaft member 73, which are joined through the friction press-contact as illustrated in FIG. 23 and FIG. 24 or joined by welding as illustrated in FIG. 25 as described above, are joined at an intermediate position on the entire shaft section having a shape and dimensions different for each vehicle type. Accordingly, as described later, it was proved that there is also a problem in terms of cost reduction achieved through enhancement of productivity and standardization of a product type of the cup member.

In addition, through the laser welding and the electron beam welding, a weld bead can be prevented from being increased in thickness, and hence the total inspection through the ultrasonic flaw detection can be performed. However, the inventors of the present invention have focused on the fact that the outer joint member is a component of the constant velocity universal joint being a mass-produced product for automobiles and the like, thereby being essential to enhance accuracy and operability in inspection on the welded portion.

The present invention has been proposed in view of the above-mentioned problems, and has an object to provide a method of manufacturing an outer joint member and an outer joint member, which are capable of increasing strength of a welded portion and quality, enhancing accuracy and operability in inspection, reducing welding cost, achieving cost reduction through enhancement of productivity and standardization of a product type, and reducing a burden of production management.

Solutions to the Problems

In order to achieve the above-mentioned object, the inventors of the present invention have diligently conducted research and verification to arrive at the following findings. Based on the findings from multiple aspects, the inventors of the present invention have conceived a novel manufacturing concept in consideration of mass-productivity to achieve the present invention.

(1) In terms of production technology, when the cup member and the shaft member are welded to each other under a state in which the cup member and the shaft member are placed in a sealed space and the hollow cavity portion as well as the sealed space is evacuated, blowing of a molten material and generation of air bubbles are suppressed.

(2) Further, in terms of productivity, when welding is performed on the cup member and the shaft member after being subjected to heat treatment such as quenching and tempering in order to enhance productivity, a temperature of a peripheral portion is increased by heat generated during the welding, which causes a risk of reduction in hardness of a region subjected to heat treatment. To address this problem, the inventors of the present invention have focused on a joining method involving steps capable of achieving highest efficiency and greatest cost reduction without affecting the joint function through change in the order of the welding step. For example, the following steps are adopted. In a case of a cup member and a shaft member having no risk of thermal effect during the welding, the cup member and the shaft member in a finished state after being subjected to heat treatment that involves quenching and tempering are welded to each other. In a case of a cup member and a shaft member having a risk of thermal effect, on the other hand, the cup member and the shaft member are subjected to heat treatment after the welding. As in this example, the inventors of the present invention have found a concept of adopting optimum steps depending on shapes, specifications, and the like of the cup member and the shaft member.

(3) Still further, in terms of productivity and standardization of the product type, the inventors of the present invention have found the following problem with the cup member 72 illustrated in FIG. 23 to FIG. 25. That is, the cup member 72 has a short shaft section formed by forging or the like to have a diameter smaller than that of the bottom portion of the cup section. This short shaft section is prepared based on the shape and dimensions of the shaft member 73, and is joined to the shaft member 73 at an intermediate position on the entire shaft section. Depending on a vehicle to which the shaft member 73 is assembled, the shaft member 73 is required to have a variety of shaft diameters and outer peripheral shapes in addition to differences in types such as a general length stem type and a long stem type. Therefore, when the short shaft section of the cup member 72 is prepared based on the shape and dimensions of the shaft member 73, and is joined to the shaft member 73 at the intermediate position on the entire shaft section, a cup member 72 dedicated to one type of the shaft member 73 is required due to differences both in shaft diameter (joining diameter) and in shape and length (joining position) of the short shaft section of the cup member 72 to be joined to the shaft member 73. Therefore, it was proved that there is a problem also in terms of cost reduction achieved through enhancement of productivity and standardization of a product type of the cup member.

(4) In addition, the inventors of the present invention have found that, in order to practically achieve the novel manufacturing concept for the outer joint member of the constant velocity universal joint being a mass-produced product for automobiles and the like, it is necessary to elaborate an ultrasonic flaw detection-inspection method and a shape of the welded portion so that accuracy and operability in inspection on the welded portion can be enhanced.

As a technical measure to achieve the above-mentioned object, according to one embodiment of the present invention, there is provided a method of manufacturing an outer joint member of a constant velocity universal joint, which is constructed by forming, through use of separate members, a cup section having track grooves formed at an inner periphery of the cup section and engageable with torque transmitting elements, and a shaft section formed at a bottom portion of the cup section, and by welding a cup member forming the cup section and a shaft member forming the shaft section, the method comprising: forming the cup member and the shaft member of medium carbon steel; preparing, as the cup member, a cup member having a cylindrical portion and a bottom portion integrally formed by forging, and a joining end surface formed on an outer surface of the bottom portion in a machining step after the forging; preparing, as the shaft member, a shaft member having a joining end surface to be joined to the bottom portion of the cup member, which is formed in a machining step; bringing the joining end surface of the cup member and the joining end surface of the shaft member into abutment against each other; welding the cup member and the shaft member by radiating a beam from an outer side of the cup member to an abutment portion between the cup member and the shaft member in a radial direction of the cup member, the joining end surface of the cup member having an outer diameter set to an equal dimension for each joint size, the welding being performed under a state in which a protruding surface protruding to a radially inner side with respect to an inner diameter of another one of the joining end surface of the cup member and the joining end surface of the shaft member is formed on a radially inner side of any one of the joining end surface of the cup member and the joining end surface of the shaft member; and performing, after the welding, ultrasonic flaw detection-inspection from any one of a surface side of the cup member and a surface side of the shaft member, which has the another one of the joining end surface of the cup member and the joining end surface of the shaft member.

Further, according to one embodiment of the present invention for an outer joint member, there is provided an outer joint member of a constant velocity universal joint, comprising: a cup section having track grooves formed at an inner periphery of the cup section and engageable with torque transmitting elements; and a shaft section formed at a bottom portion of the cup section, the other joint member being constructed by forming the cup section and the shaft section through use of separate members, and by welding a cup member forming the cup section and a shaft member forming the shaft section, the cup member and the shaft member being formed of medium carbon steel, the cup member having a cylindrical portion and a bottom portion integrally formed by forging, and a joining end surface formed on an outer surface of the bottom portion, the shaft member having a joining end surface formed at an end portion of the shaft member to be joined to the bottom portion of the cup member, the cup member and the shaft member being welded to each other under a state in which the joining end surface of the cup member and the joining end surface of the shaft member are held in abutment against each other, the outer joint member comprising a welded portion between the cup member and the shaft member, which is formed of a bead formed by a beam radiated in a radial direction of the cup member from an outer side of the cup member, the joining end surface of the cup member having an outer diameter set to an equal dimension for each joint size, the outer joint member comprising a protruding surface protruding to a radially inner side with respect to an inner diameter of another one of the joining end surface of the cup member and the joining end surface of the shaft member, the protruding surface being formed on a radially inner side of any one of the joining end surface of the cup member and the joining end surface of the shaft member, the cup member and the shaft member being welded to each other under a state in which the protruding surface is formed.

With the above-mentioned configuration, it is possible to achieve the method of manufacturing an outer joint member and the outer joint member, which are capable of increasing the strength of the welded portion and the quality, reducing the welding cost, enhancing the accuracy and the operability in the inspection on the welded portion, achieving the cost reduction through the enhancement of productivity of the cup member and the shaft member and through the standardization of a product type of the cup member, and reducing the burden of production management.

Specifically, it is preferred that the above-mentioned ultrasonic flaw detection-inspection comprise performing the flaw detection under a state in which the cup member and the shaft member after the welding are placed under water. With this configuration, the accuracy in the inspection can be further enhanced.

When the above-mentioned protruding surface is formed into the same shape for each joint size, and when the protruding surface is formed on the joining end surface of the cup member, a degree of processing for the cup member to be standardized in product type can be increased. As a result, the enhancement of productivity and the reduction of the burden of production management can be further promoted. Further, at the time of ultrasonic flaw-detection inspection on the welded portion, an ultrasonic wave from an angle probe is input from a surface side of the shaft member having a small shaft diameter. Thus, the flaw-detection inspection can be facilitated.

In this case, in Claims and Specification of the present invention, setting the outer diameter of the joining end surface of the cup member to an equal dimension for each joint size, and forming the protruding surface into the same shape for each joint size are not limited to preparing one type of the cup member for one joint size, that is, not limited to preparing the cup member assigned with a single product number. For example, the present invention encompasses preparing cup members of a plurality of types (assigned with a plurality of product numbers, respectively) for one joint size based on different specifications of a maximum operating angle, setting the outer diameter of the joining end surface of each of the cup members to an equal dimension, and forming the protruding surface into the same shape. In addition, the present invention encompasses, for example, preparing cup members of a plurality of types (assigned with a plurality of product numbers, respectively) for one joint size in order to achieve management of the cup members in a plurality of forms including intermediate components before heat treatment and finished components after heat treatment in consideration of the joint function, the circumstances at the manufacturing site, the productivity, and the like, setting the outer diameter of the joining end surface of each of the cup members to an equal dimension, and forming the protruding surface into the same shape.

Further, in Claims and Specification of the present invention, setting the outer diameter of the joining end surface of the cup member to an equal dimension for each joint size, and forming the protruding surface into the same shape for each joint size may be applied also to different types of constant velocity universal joints. For example, the present invention encompasses setting outer diameters of the joining end surfaces of a tripod type constant velocity universal joint and a double-offset constant velocity universal joint to equal dimensions, and forming the protruding surface into the same shape on the inboard side, and encompasses setting outer diameters of the joining end surfaces of a Rzeppa type constant velocity universal joint and an undercut-free type constant velocity universal joint to equal dimensions, and forming the protruding surface into the same shape on the outboard side. Further, the present invention also encompasses setting the outer diameters of the joining end surfaces of the constant velocity universal joints on the inboard side and the outboard side to equal dimensions, and forming the protruding surface into the same shape on the inboard side and the outboard side.

At least one of the cup member or the shaft member before the welding may be prepared as an intermediate component without performing heat treatment. In this case, the heat treatment and finishing such as grinding and quenched-steel cutting work are performed after the welding. Thus, this configuration is suited to a cup member and a shaft member having such shapes and specifications that the hardness of the heat-treated portion may be affected by temperature rise at the periphery due to heat generated during the welding. The intermediate component is assigned with a product number for management.

Further, at least one of the cup member or the shaft member before the welding may be prepared as a finished component subjected to heat treatment. With the at least one of the cup member or the shaft member prepared as the finished component subjected to the heat treatment and the finishing such as grinding after the heat treatment or quenched-steel cutting work, it is possible to obtain the cup member prepared as the finished component for common use for each joint size, and the shaft member having a variety of specifications of the shaft section for each vehicle type. Thus, the cup member and the shaft member are each assigned with a product number for management. Therefore, the cost is significantly reduced through the standardization of a product type of the cup member, and the burden of production management is significantly alleviated. Further, the cup member prepared for common use and the shaft member having a variety of specifications of the shaft section can be manufactured separately until the cup member and the shaft member are formed into the finished components subjected to the finishing such as forging, turning, heat treatment, grinding, and quenched-steel cutting work. Further, as well as reduction of setups and the like, the enhancement of productivity is achieved. However, the cup member and the shaft member as the finished components are not limited to members subjected to finishing such as the grinding after the heat treatment or the quenched-steel cutting work as described above. The cup member and the shaft member according to the present invention encompass members assuming a state after completion of heat treatment but before being subjected to the finishing.

The above-mentioned welding comprises electron beam welding. Thus, burrs are not generated on the joining portion. Reduction of manufacturing cost through omission of the number of steps of post-processing for the joining portion can be reliably achieved, and further, total inspection on the joining portion through ultrasonic flaw detection can be more reliably performed. Further, deep penetration can be obtained by electron beam welding, thereby being capable of increasing welding strength and reducing thermal strain.

It is desired that the cup member and the shaft member be welded to each other under a state in which the cup member and the shaft member are placed in a sealed space to keep a pressure equal to or less than an atmospheric pressure. Accordingly, the blowing of a molten material and the generation of air bubbles are suppressed, thereby enhancing the strength and quality of the welded portion.

It is desired that a hardness of a welded portion between the cup member and the shaft member range from 200 Hv to 500 Hv. When the hardness is lower than 200 Hv, it is difficult to secure the strength required in terms of a product function, which is undesirable. On the other hand, when the hardness exceeds 500 Hv, there may occur cracking due to phase transformation and degradation of fatigue strength due to changes in toughness, which are undesirable.

Effects of the Invention

According to the method of manufacturing an outer joint member of a constant velocity universal joint and the outer joint member of the present invention, it is possible to achieve the method of manufacturing an outer joint member and the outer joint member, which are capable of increasing the strength of the welded portion and the quality, reducing the welding cost, enhancing the accuracy and the operability in the inspection on the welded portion, achieving the cost reduction through the enhancement of productivity of the cup member and the shaft member and through the standardization of a product type of the cup member, and reducing the burden of production management.

BRIEF DESCRIPTION OF DRAWINGS

FIG. 2a is an enlarged partial vertical sectional view for illustrating the outer joint member of FIG. 1.

FIG. 2b is an enlarged view for illustrating a welded portion of FIG. 2a.

FIG. 2c is an enlarged view for illustrating a shape before welding in FIG. 2b.

FIG. 5a is a front view for illustrating a shaft member before welding, that is, a bar material being a blank.

FIG. 5b is a partial vertical sectional view for illustrating the shaft member before welding and after forging.

FIG. 5c is a partial vertical sectional view for illustrating the shaft member before welding and after turning and spline processing.

FIG. 17a is a partial vertical sectional view for illustrating a modification of the outer joint member according to the first embodiment.

FIG. 17b is an enlarged view for illustrating a welded portion of FIG. 17a.

FIG. 17c is an enlarged view for illustrating a shape before welding in FIG. 17b.

EMBODIMENTS OF THE INVENTION

Now, description is made of embodiments of the present invention with reference to the drawings.

Figure 1:
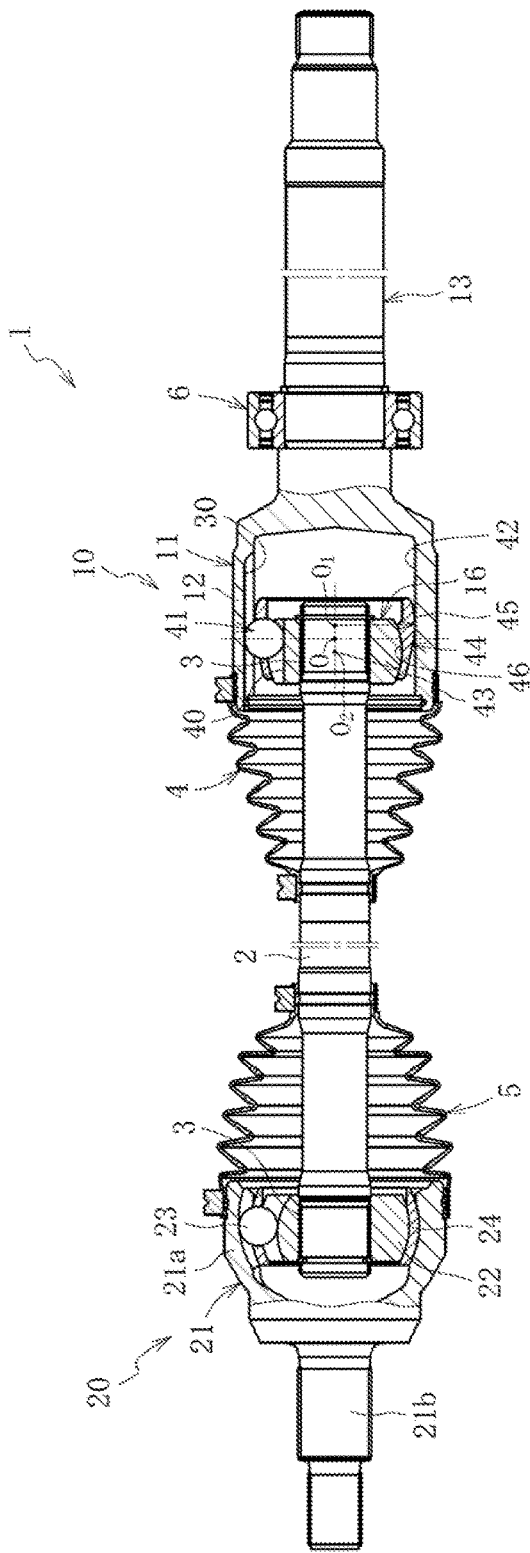
FIG. 1 is a view for illustrating the entire structure of a drive shaft to which an outer joint member according to a first embodiment of the present invention is applied.
Figure 2:
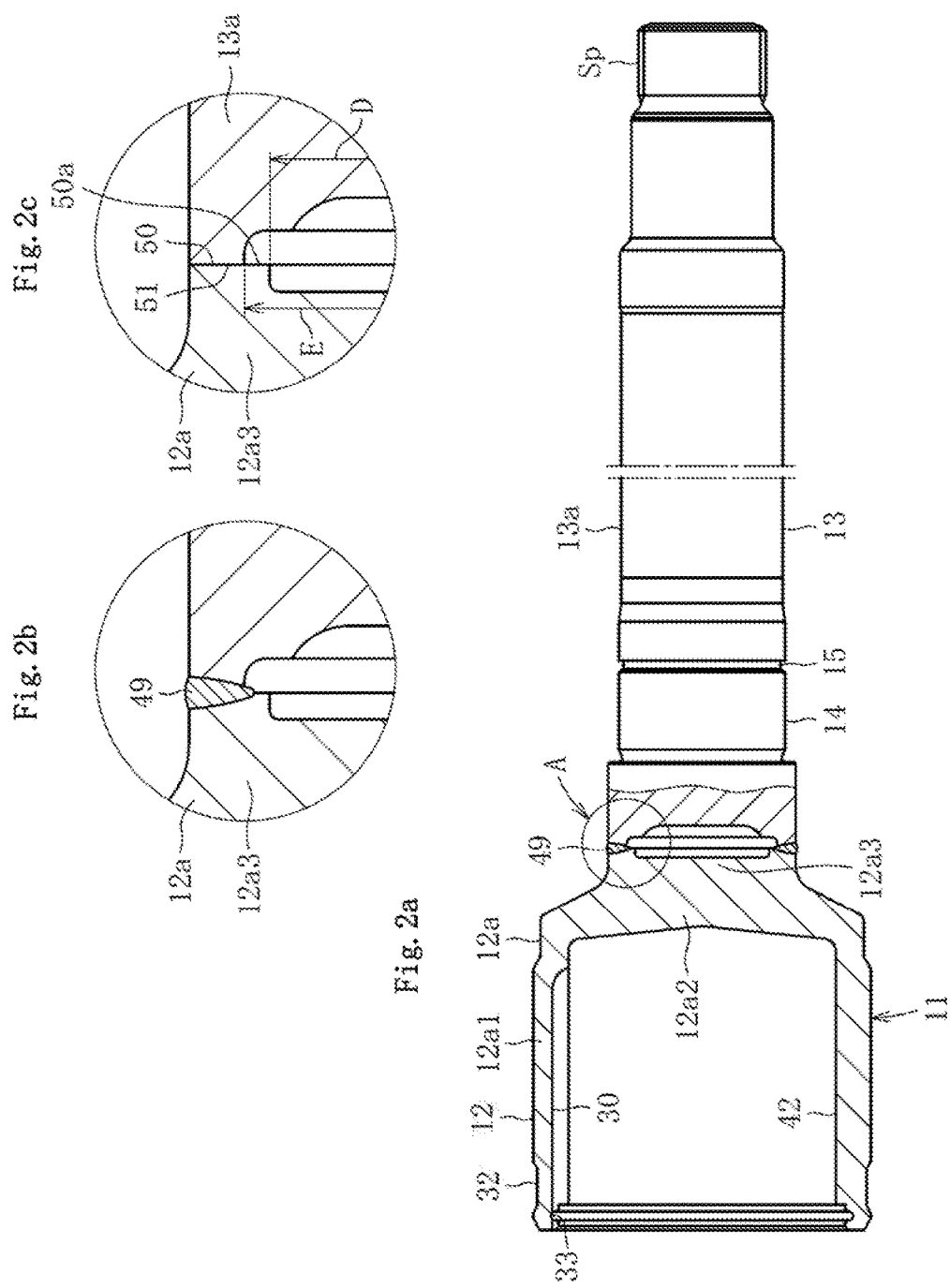

FIG. 3 to FIG. 16 are views for illustrating a method of manufacturing an outer joint member of a constant velocity universal joint according to a first embodiment of the present invention, and FIG. 1 and FIG. 2 are views for illustrating an outer joint member according to the first embodiment of the present invention. First, the outer joint member according to the first embodiment is described with reference to FIG. 1 and FIG. 2, and subsequently, the method of manufacturing an outer joint member according to the first embodiment is described with reference to FIG. 3 to FIG. 16.

FIG. 1 is a view for illustrating the entire structure of a drive shaft 1 using an outer joint member 11 according to the first embodiment. The drive shaft 1 mainly comprises a plunging type constant velocity universal joint 10 arranged on a differential side (right side of FIG. 1: hereinafter also referred to as "inboard side"), a fixed type constant velocity universal joint 20 arranged on a driving wheel side (left side of FIG. 1: hereinafter also referred to as "outboard side"), and an intermediate shaft 2 configured to couple both the constant velocity universal joints 10 and 20 to allow torque transmission therebetween.

The plunging type constant velocity universal joint 10 illustrated in FIG. 1 is a so-called double-offset type constant velocity universal joint (DOJ). The constant velocity universal joint 10 comprises the outer joint member 11 comprising a cup section 12 and a long shaft section (hereinafter referred to also as "long stem section") 13 that extends from a bottom portion of the cup section 12 in an axial direction, an inner joint member 16 housed along an inner periphery of the cup section 12 of the outer joint member 11, balls 41 serving as torque transmitting elements that are arranged between track grooves 30 and 40 of the outer joint member 11 and the inner joint member 16, and a cage 44 having a spherical outer peripheral surface 45 and a spherical inner peripheral surface 46 that are fitted to a cylindrical inner peripheral surface 42 of the outer joint member 11 and a spherical outer peripheral surface 43 of the inner joint member 16, respectively, and being configured to retain the balls 41. A curvature center $O_1$ of the spherical outer peripheral surface 45 and a curvature center $O_2$ of the spherical inner peripheral surface 46 of the cage 44 are offset equidistantly from a joint center O toward opposite sides in the axial direction.

An inner ring of a support bearing 6 is fixed to an outer peripheral surface of the long stem section 13, and an outer ring of the support bearing 6 is fixed to a transmission case with a bracket (not shown). The outer joint member 11 is supported by the support bearing 6 in a freely rotatable manner, and when the support bearing 6 as described above is provided, vibration of the outer joint member 11 during driving or the like is prevented as much as possible.

The fixed type constant velocity universal joint 20 illustrated in FIG. 1 is a so-called Rzeppa type constant velocity universal joint, and comprises an outer joint member 21 comprising a bottomed cylindrical cup section 21a and a shaft section 21b that extends from a bottom portion of the cup section 21a in the axial direction, an inner joint member 22 housed along an inner periphery of the cup section 21a of the outer joint member 21, balls 23 serving as torque transmitting elements that are arranged between the cup section 21a of the outer joint member 21 and the inner joint member 22, and a cage 24, which is arranged between an inner peripheral surface of the cup section 21a of the outer joint member 21 and an outer peripheral surface of the inner joint member 22, and is configured to retain the balls 23. Note that, as the fixed type constant velocity universal joint 20, an undercut-free type constant velocity universal joint may sometimes be used.

The intermediate shaft 2 comprises splines 3 for torque transmission (including serrations; the same applies hereinafter) at outer peripheries on both end portions thereof. The spline 3 on the inboard side is spline-fitted to a hole portion of the inner joint member 16 of the plunging type constant velocity universal joint 10. Thus, the intermediate shaft 2 and the inner joint member 16 of the plunging type constant velocity universal joint 10 are coupled to each other to allow torque transmission therebetween. Further, the spline 3 on the outboard side is spline-fitted to a hole portion of the inner joint member 22 of the fixed type constant velocity universal joint 20. Thus, the intermediate shaft 2 and the inner joint member 22 of the fixed type constant velocity universal joint 20 are coupled to each other to allow torque transmission therebetween. Although the solid intermediate shaft 2 is illustrated, a hollow intermediate shaft may be used instead.

Grease is sealed inside both the constant velocity universal joints 10 and 20 as a lubricant. To prevent leakage of the grease to an outside of the joint or entry of a foreign matter from the outside of the joint, bellows boots 4 and 6 are respectively mounted to a portion between the outer joint member 11 of the plunging type constant velocity universal joint 10 and the intermediate shaft 2 and a portion between the outer joint member 21 of the fixed type constant velocity universal joint 20 and the intermediate shaft 2.

The outer joint member according to the first embodiment is described with reference to FIG. 2. FIG. 2 are enlarged views for illustrating the outer joint member 11 according to this embodiment. FIG. 2a is a partial vertical sectional view. FIG. 2b is an enlarged view for illustrating a circle "A" of FIG. 2a. FIG. 2c is a view for illustrating a shape before welding. The outer joint member 11 comprises the bottomed cylindrical cup section 12 that is opened at one end and has the cylindrical inner peripheral surface 42 and the plurality of track grooves 30, on which the balls 41 (see FIG. 1) are caused to roll, formed equiangularly on the inner peripheral surface, and the long stem section 13 that extends from the bottom portion of the cup section 12 in the axial direction and comprises a spline Sp serving as a torque transmitting coupling portion formed at an outer periphery on an end portion thereof on an opposite side to the cup section 12. In this embodiment, the outer joint member 11 is formed by welding a cup member 12a and a shaft member 13a to each other.

The cup member 12a illustrated in FIG. 2a to FIG. 2c is an integrally-formed product being made of medium carbon steel, such as S53C, containing carbon of from 0.40 wt % to 0.60 wt %, and having a cylindrical portion 12a1 and a bottom portion 12a2. The cylindrical portion 12a1 has the track grooves 30 and the cylindrical inner peripheral surface 42 formed at an inner periphery thereof. A projecting portion 12a3 is formed at the bottom portion 12a2 of the cup member 12a. A boot mounting groove 32 is formed at an outer periphery of the cup member 12a on the opening side thereof, whereas a snap ring groove 33 is formed at an inner periphery of the cup member 12a on the opening side thereof. A bearing mounting surface 14 and a snap ring groove 15 are formed at an outer periphery of the shaft member 13a on the cup member 12a side, whereas the spline Sp is formed at an end portion of the shaft member 13a on an opposite side.

The shaft member 13a is made of medium carbon steel, such as S40C, containing carbon of from 0.30 wt % to 0.55 wt %. A joining end surface 50 formed at the projecting portion 12a3 of the bottom portion 12a2 of the cup member 12a and a joining end surface 51 formed at an end portion of the shaft member 13a on the cup member 12a side are brought into abutment against each other, and are welded to each other by electron beam welding performed from an outer side of the cup member 12a in a radial direction. As illustrated in FIG. 2a and FIG. 2b, a welded portion 49 is formed of a bead, which is formed by a beam radiated from a radially outer side of the cup member 12a. Although detailed description is made later, outer diameters B of the joining end surface 50 and the joining end surface 51 (see FIG. 4b and FIG. 5c) are set to equal dimensions for each joint size. However, the outer diameter B of the joining end surface 50 of the cup member 12a and the outer diameter B of the joining end surface 51 of the shaft member 13a need not be set to equal dimensions. In consideration of for example, a state of the weld bead, a dimensional difference may be given as appropriate in such a manner that the outer diameter B of the joining end surface 51 is set slightly smaller than the outer diameter B of the joining end surface 50 (the dimensional relationship between the outer diameter B of the joining end surface 50 and the outer diameter B of the joining end surface 51 is consistent throughout specification.

The welded portion 49 is formed on the joining end surface 51 located on the cup member 12a side with respect to the bearing mounting surface 14 of the shaft member 13a, and hence the bearing mounting surface 14 and the like can be processed in advance so that post-processing after welding can be omitted. Further, due to the electron beam welding, burrs are not generated at the welded portion. Thus, post-processing for the welded portion can also be omitted, which can reduce manufacturing cost. Still further, total inspection on the welded portion through ultrasonic flaw detection can be performed. Note that, features of this embodiment reside in an ultrasonic flaw detection-inspection method and a shape of the welded portion, which are capable of enhancing accuracy and operability in inspection on the welded portion in order to practically achieve the novel manufacturing concept for the outer joint member of the constant velocity universal joint being a mass-produced product. Details thereof are described later.

As illustrated in FIG. 2c, an inner diameter D of the joining end surface 50 of the cup member 12a is set smaller than an inner diameter E of the joining end surface 51 of the shaft member 13a. On the joining end surface 50 of the cup member 12a, a protruding surface 50a protruding to a radially inner side with respect to the inner diameter E of the joining end surface 51 of the shaft member 13a is formed. In such a state, the cup member 12a and the shaft member 13a are welded to each other. The protruding surface 50a is formed into the same shape for each joint size.

Figure 3:
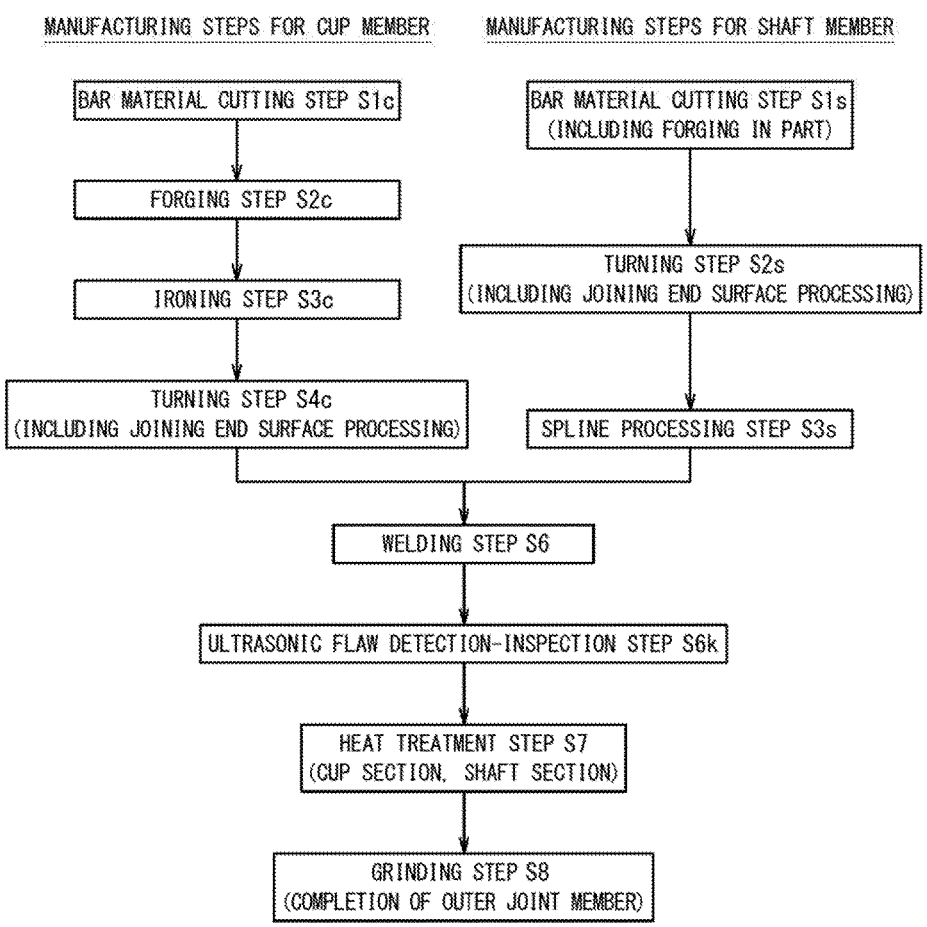
FIG. 3 is a diagram for illustrating an overview of manufacturing steps for the outer joint member of FIG. 1.

Next, the manufacturing method according to the first embodiment of the present invention is described with reference to FIG. 3 to FIG. 16. Before description of details of the features of the manufacturing method of this embodiment, that is, an ultrasonic flaw detection-inspection step for the welded portion, an overview of manufacturing steps (processing steps) is described. FIG. 3 is an illustration of the overview of the manufacturing steps for the outer joint member. In this embodiment, as illustrated in FIG. 3, the cup member 12a is manufactured through manufacturing steps comprising a bar material cutting step S1c, a forging step S2c, an ironing step S3c, and a turning step S4c. On the other hand, the shaft member 13a is manufactured through manufacturing steps comprising a bar material cutting step S1s, a turning step S2s, and a spline processing step S3s. Intermediate components of the cup member 12a and the shaft member 13a thus manufactured are each assigned with a product number for management.

After that, the cup member 12a and the shaft member 13a are subjected to a welding step S6, an ultrasonic flaw detection-inspection step S6K, a heat treatment step S7, and a grinding step S8 so that the outer joint member 11 is completed. A machining step described in Claims refers to the turning step S4c and the turning step S2s among the above-mentioned manufacturing steps, and to a grinding step S5s described later (see FIG. 20).

An overview of each step is described. Each step is described as a typical example, and appropriate modification and addition may be made to each step as needed. First, the manufacturing steps for the cup member 12a are described.

[Bar Material Cutting Step S1c]

A bar material is cut into a predetermined length in accordance with a forging weight, thereby producing a billet.

[Forging Step S2c]

The billet is subjected to forging so as to integrally form the cylindrical portion, the bottom portion, and the projecting portion as a preform of the cup member 12a.

[Ironing Step S3c]

Ironing is performed on the track grooves 30 and the cylindrical inner peripheral surface 42 of the preform, thereby finishing the inner periphery of the cylindrical portion of the cup member 12a.

[Turning Step S4c]

In the preform after ironing, the outer peripheral surface, the boot mounting groove 32, the snap ring groove 33 and the like, and the joining end surface 50 are formed by turning. In this embodiment, after the turning step S4c, the cup member 12a in the form of an intermediate component is assigned with a product number for management.

Next, the manufacturing steps for the shaft member 13a are described.

[Bar Material Cutting Step S1s]

A bar material is cut into a predetermined length in accordance with the total length of the shaft section, thereby producing a billet. After that, the billet may be forged into a rough shape by upset forging depending on the shape of the shaft member 13a.

[Turning Step S2s]

The outer peripheral surface of the billet (bearing mounting surface 14, snap ring groove 15, minor diameter of the spline, end surface, and the like) and the joining end surface 51 of the billet at the end portion on the cup member 12a side are formed by turning.

[Spline Processing Step S3s]

The spline is formed by rolling in the shaft member after turning. Note that, the method of processing the spline is not limited to the rolling, but press working or the like may be adopted instead as appropriate. In this embodiment, after the spline processing, the shaft member 13a in the form of an intermediate component is assigned with a product number for management.

Next, the manufacturing steps in the process of completing the outer joint member 11 from the cup member 12a and the shaft member 13a are described.

[Welding Step S6]

The joining end surface 50 of the cup member 12a and the joining end surface 51 of the shaft member 13a are brought into abutment against and welded to each other.

[Ultrasonic Flaw Detection-Inspection Step S6k]

The welded portion 49 between the cup member 12a and the shaft member 13a is inspected by the ultrasonic flaw-detection method.

[Heat Treatment Step S7]

Induction quenching and tempering are performed as heat treatment on at least the track grooves 30 and the cylindrical inner peripheral surface 42 of the cup section 12 after welding and a necessary range of the outer periphery of the shaft section 13 after welding. Heat treatment is not performed on the welded portion. A hardened layer having a hardness of approximately from 58 HRC to 62 HRC is formed on each of the track grooves 30 and the cylindrical inner peripheral surface 42 of the cup section 12. Further, a hardened layer having a hardness of approximately from 50 HRC to 62 HRC is formed in a predetermined range of the outer periphery of the shaft section 13.

[Grinding Step S8]

After the heat treatment, the bearing mounting surface 14 of the shaft section 13 and the like are finished by grinding. Thus, the outer joint member 11 is completed.

In the manufacturing steps of this embodiment, the heat treatment step is provided after the welding step, and hence the manufacturing steps are suited to a cup member and a shaft member having such shapes and specifications that the hardness of the heat-treated portion may be affected by temperature rise at the periphery due to heat generated during the welding.

Figure 4A:
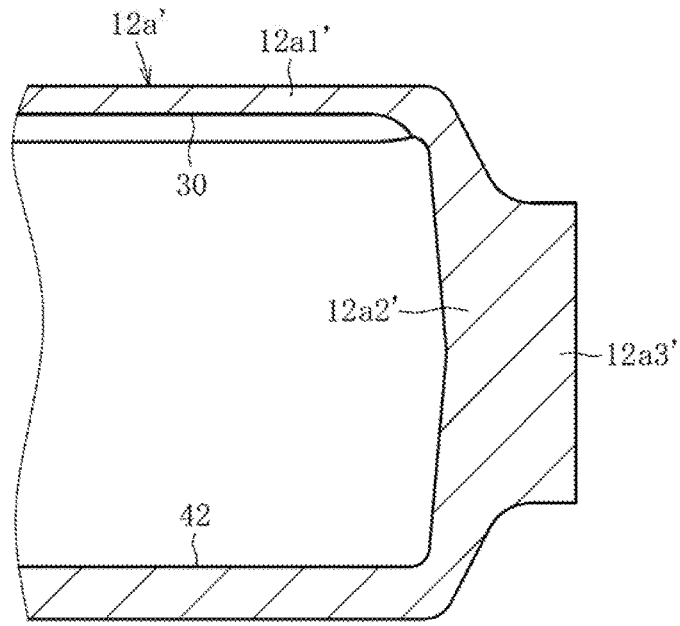
FIG. 4a is a vertical sectional view for illustrating a cup member before welding and after ironing.
Figure 4B:
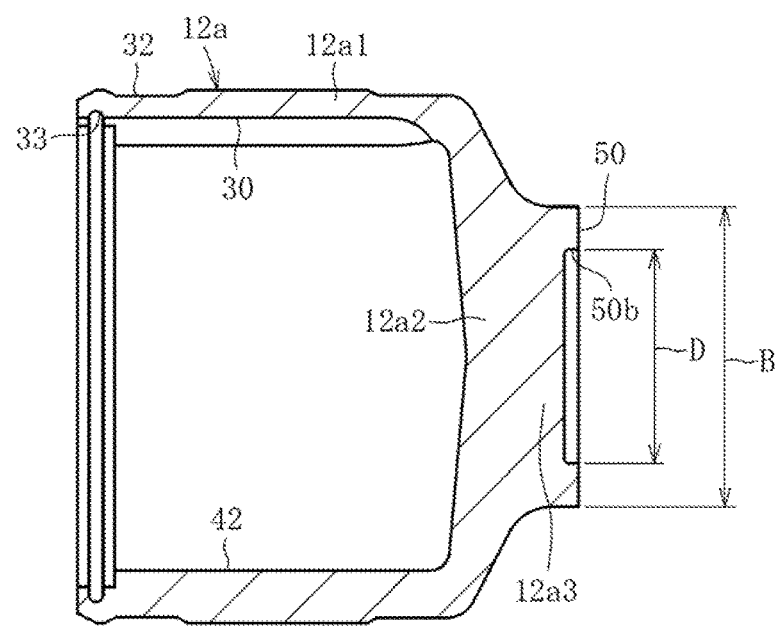
FIG. 4b is a vertical sectional view for illustrating the cup member before welding and after turning.

Next, main constituent features of the manufacturing method of this embodiment are described in detail. FIG. 4a is a vertical sectional view for illustrating a state after ironing of the cup member 12a. FIG. 4b is a vertical sectional view for illustrating a state after turning. In a preform 12a' for the cup member 12a, a cylindrical portion 12a1', a bottom portion 12a2', and a projecting portion 12a3' are integrally formed in the forging step S2c. After that, the track grooves 30 and the cylindrical inner peripheral surface 42 are formed by ironing in the ironing step S3c so that the inner periphery of the cylindrical portion 12a1' is finished as illustrated in FIG. 4a.

After that, in the turning step S4c, the outer peripheral surface, the boot mounting groove 32, the snap ring groove 33, and the like of the cup member 12a as well as the joining end surface 50 of the projecting portion 12a3 of the bottom portion 12a2 and the joining end surface 50 having the outer diameter B and the inner diameter D are formed by turning as illustrated in FIG. 4b.

FIG. 5 are illustrations of states of the shaft member 13a in the respective processing steps. FIG. 5a is a front view for illustrating a billet 13a" obtained by cutting a bar material. FIG. 5b is a partial vertical sectional view for illustrating a preform 13a' obtained by forging the billet 13a" into a rough shape by upset forging. FIG. 5c is a partial vertical sectional view for illustrating the shaft member 13a after turning and spline processing.

The billet 13a" illustrated in FIG. 5a is produced in the bar material cutting step S1s. The preform 13a' is produced by increasing, if necessary, the shaft diameter of the billet 13a" in a predetermined range and forming a recessed portion 52 at a joining-side end portion (end portion on the cup member 12a side) by upset forging as illustrated in FIG. 5b.

After that, in the turning step S2s, the outer diameter of the shaft member 13a, the bearing mounting surface 14, the snap ring groove 16, an inner diameter portion 53 (inner diameter E) of the recessed portion 52, the joining end surface 51, and the joining end surface 50 having the outer diameter B are formed by turning as illustrated in FIG. 5c. In the spline processing step S3s, the spline Sp is processed at the end portion on the opposite side to the recessed portion 52 by rolling or press forming.

The outer diameter B of the joining end surface 50 located at the projecting portion 12a3 of the bottom portion 12a2 of the cup member 12a illustrated in FIG. 4b is set to an equal dimension for one joint size. Further, in the shaft member 13a illustrated in FIG. 5c, which is used as a long stem shaft, the outer diameter B of the joining end surface 51 located at the end portion on the cup member 12a side is set to an equal dimension to the outer diameter B of the joining end surface 50 of the cup member 12a irrespective of the shaft diameter and the outer peripheral shape. Still further, the joining end surface 51 of the shaft member 13a is located at the position on the cup member 12a side with respect to the bearing mounting surface 14. Through the setting of dimensions as described above, the outer joint member 11 compatible with various vehicle types can be manufactured in such a manner that, while the cup member 12a is prepared for common use, only the shaft member 13a is manufactured to have a variety of shaft diameters, lengths, and outer peripheral shapes depending on vehicle types, and both the members 12a and 13a are welded to each other. Details of the preparation of the cup member 12a for common use are described later.

Figure 6:
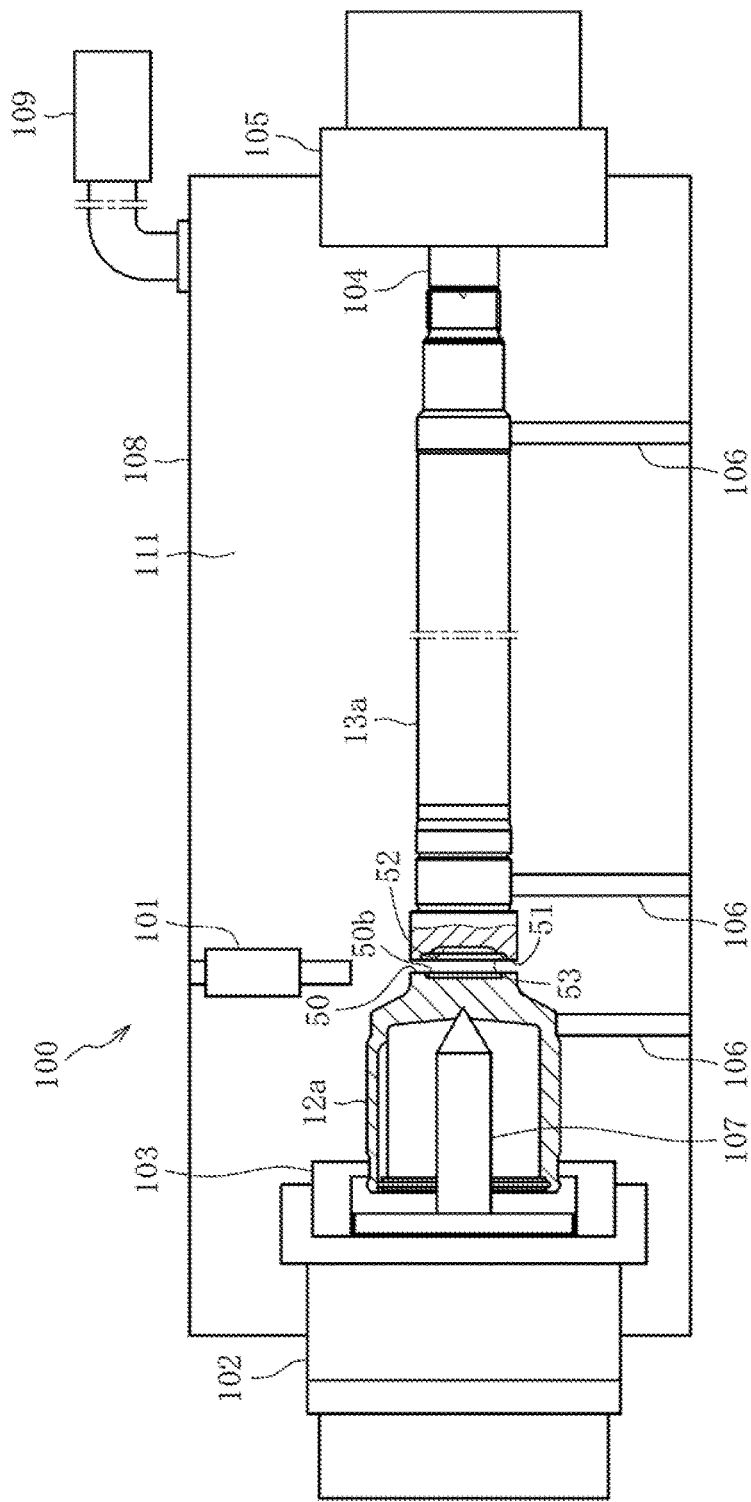
FIG. 6 is a view for illustrating an overview of a welding step.
Figure 7:
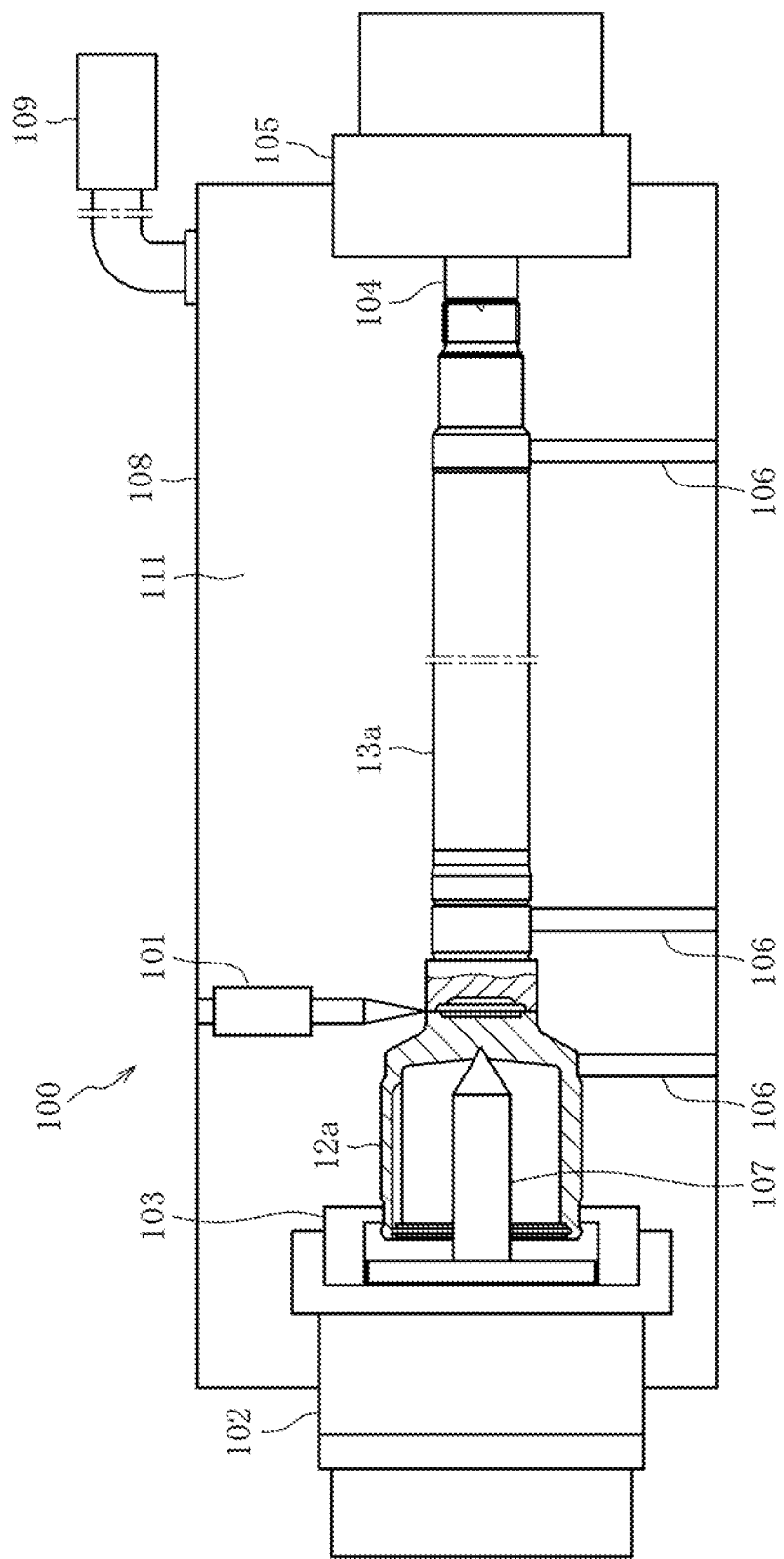
FIG. 7 is a view for illustrating an overview of the welding step.

Next, a method of welding the cup member 12a and the shaft member 13a is described with reference to FIG. 6 and FIG. 7. FIG. 6 and FIG. 7 are views for illustrating an overview of a welding apparatus. FIG. 6 is an illustration of a state before welding. FIG. 7 is an illustration of a state during welding. As illustrated in FIG. 6, a welding apparatus 100 mainly comprises an electron gun 101, a rotation device 102, a chuck 103, a center hole guide 104, a tailstock 105, workpiece supports 106, a center hole guide 107, a case 108, and a vacuum pump 109.

The cup member 12a and the shaft member 13a being workpieces are placed on the workpiece supports 106 arranged inside the welding apparatus 100. The chuck 103 and the center hole guide 107 arranged at one end of the welding apparatus 100 are coupled to the rotation device 102. The chuck 103 grips the cup member 12a to rotate the cup member 12a under a state in which the center hole guide 107 has centered the cup member 12a. The center hole guide 104 is integrally mounted to the tailstock 105 arranged at the other end of the welding apparatus 100. Both the center hole guide 104 and the tailstock 106 are configured to reciprocate in the axial direction (lateral direction of FIG. 7).

A center hole of the shaft member 13a is set on the center hole guide 104 so that the shaft member 13a is centered. The vacuum pump 109 is connected to the case 108 of the welding apparatus 100. A "sealed space" herein refers to a space 111 defined by the case 108. In this embodiment, the cup member 12a and the shaft member 13a are entirely received in the sealed space 111. The electron gun 101 is arranged at a position corresponding to the joining end surfaces 50 and 51 of the cup member 12a and the shaft member 13a. The electron gun 101 is configured to approach the workpieces up to a predetermined position.

Next, the operation of the welding apparatus 100 constructed as described above and the welding method are described. The cup member 12a and the shaft member 13a being workpieces are stocked at a place different from the place of the welding apparatus 100. The respective workpieces are taken out by, for example, a robot, are conveyed into the case 108 of the welding apparatus 100 opened to the air as illustrated in FIG. 6, and are set at predetermined positions on the workpiece supports 106. At this time, the center hole guide 104 and the tailstock 105 are retreated to the right side of FIG. 6, and hence a gap is formed between the joining end surfaces 50 and 51 of the cup member 12a and the shaft member 13a. After that, a door (not shown) of the case 108 is closed and the vacuum pump 109 is activated to reduce the pressure in the sealed space 111 defined in the case 108. Thus, the pressures in an inner diameter portion 50b of the cup member 12a and the recessed portion 52 and the inner diameter portion 53 of the shaft member 13a are reduced as well.

When the pressure in the sealed space 111 is reduced to a predetermined pressure, the center hole guide 104 and the tailstock 105 are advanced to the left side as illustrated in FIG. 7 to eliminate the gap between the joining end surfaces 50 and 61 of the cup member 12a and the shaft member 13a. Thus, the cup member 12a is centered by the center hole guide 107 and fixed by the chuck 103, whereas the shaft member 13a is supported by the center hole guide 104. After that, the workpiece supports 106 are moved away from the workpieces. At this time, the distance between the workpiece supports 106 and the workpieces may be infinitesimal, and hence illustration of this distance is omitted from FIG. 7. As a matter of course, the welding apparatus 100 may have such a structure that the workpiece supports 106 are retreated downward greatly.

Although illustration is omitted, the electron gun 101 is then caused to approach the workpieces up to a predetermined position and the workpieces are rotated to start pre-heating. As a pre-heating condition, unlike the welding condition, the temperature is set lower than the welding temperature by, for example, radiating an electron beam under a state in which the electron gun 101 is caused to approach the workpieces so as to increase the spot diameter. Through the pre-heating, the cooling rate after welding is reduced, thereby being capable of preventing a quenching crack. When a predetermined pre-heating time has elapsed, the electron gun 101 is retreated to a predetermined position, and radiates the electron beam from the outer side of the workpieces in the radial direction to start welding. When the welding is finished, the electron gun 101 is retreated and the rotation of the workpieces is stopped.

Although illustration is omitted, the sealed space 111 is then opened to the air. Then, the center hole guide 104 and the tailstock 105 are retreated to the right side and the chuck 103 is opened under a state in which the workpiece supports 106 are raised to support the workpieces. After that, for example, the robot grips the workpieces, takes the workpieces out of the welding apparatus 100, and places the workpieces into alignment on a cooling stocker. In this embodiment, the cup member 12a and the shaft member 13a are entirely received in the sealed space 111, and hence the configuration of the sealed space 111 defined in the case 108 can be simplified.

Specifically, the cup member 12a having a carbon content of from 0.4% to 0.6% and the shaft member 13a having a carbon content of from 0.3% to 0.55% were used and welded to each other in the above-mentioned welding apparatus 100 under the condition that the pressure in the sealed space 111 defined in the case 108 was set to 6.7 Pa or less. In order to prevent the cup member 12a and the shaft member 13a from being cooled rapidly after the welding to suppress increase in hardness of the welded portion, the joining end surfaces 50 and 51 of the cup member 12a and the shaft member 13a were soaked by pre-heating to have a temperature of from 300° C. to 650° C., and then electron beam welding was performed. As a result, a welded portion having a projecting height from the welded surface (0.5 mm or less), which imposed no adverse effect on a product function, was obtained. Further, through the soaking by pre-heating, the hardness of the welded portion after completion of the welding was able to be kept within a range of from 200 Hv to 500 Hv, thereby being capable of attaining high welding strength and stable welding state and quality. Still further, the cup member 12a and the shaft member 13a were welded to each other under the condition that the pressure in the sealed space ill of the welding apparatus 100 was set to an atmospheric pressure or less, thereby being capable of suppressing the change in pressure in the hollow cavity portion during the welding. As a result, the blowing of a molten material and the entry of the molten material toward the radially inner side were able to be prevented.

Figure 8:
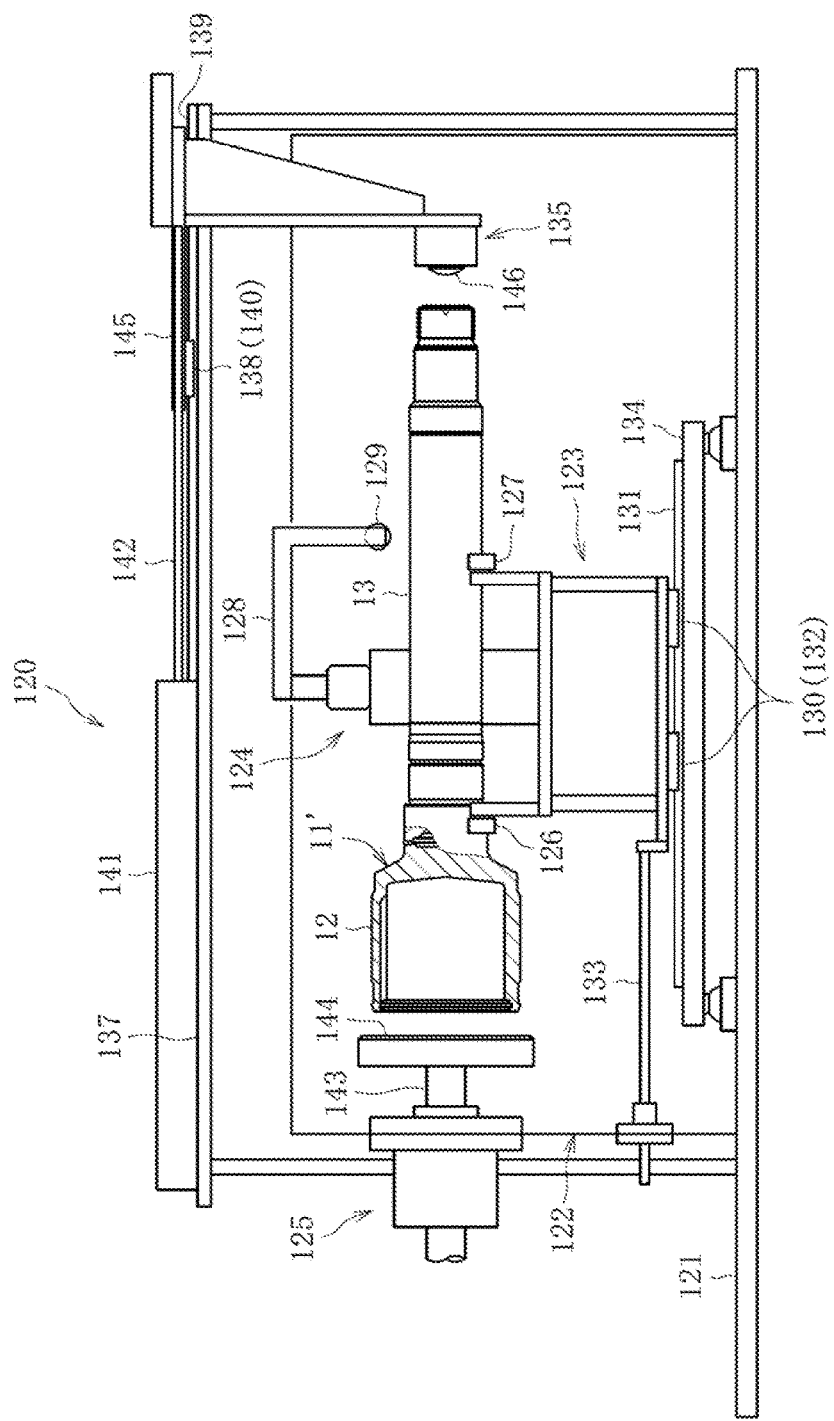
FIG. 8 is a front view for illustrating an overview of an ultrasonic flaw detection-inspection apparatus.
Figure 9:
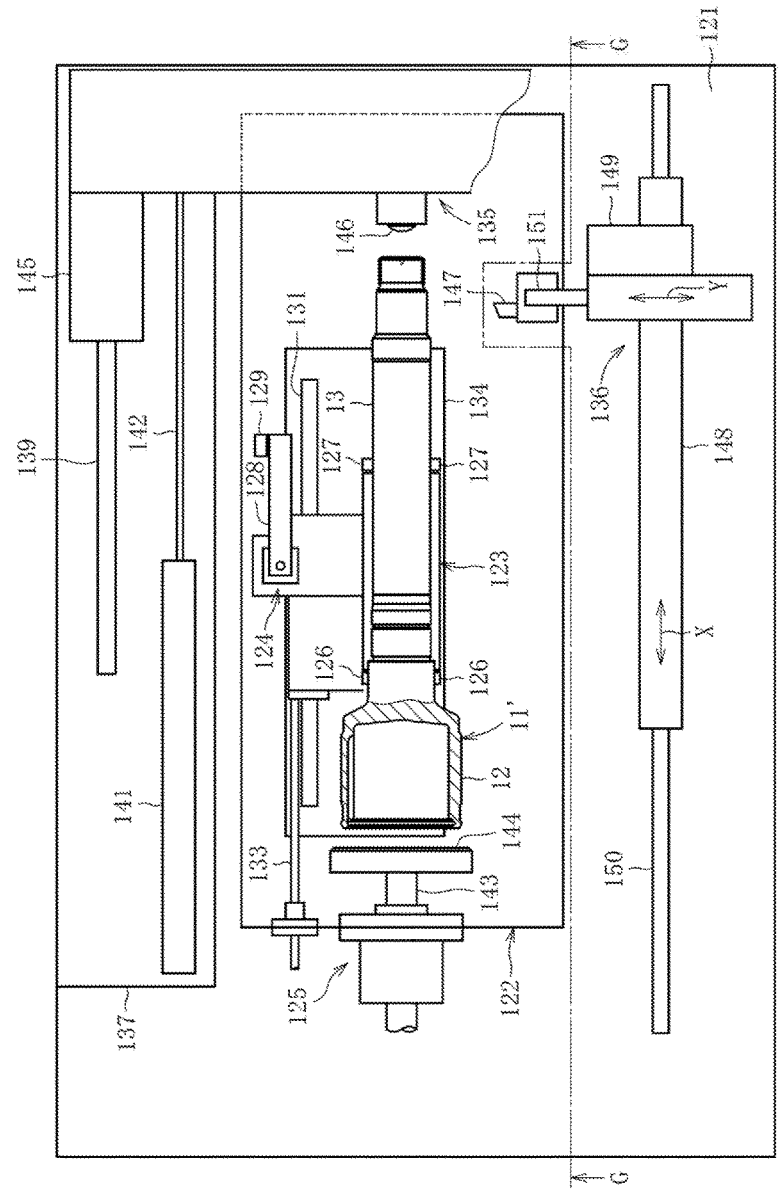
FIG. 9 is a plan view for illustrating the overview of the ultrasonic flaw detection-inspection apparatus.
Figure 10:
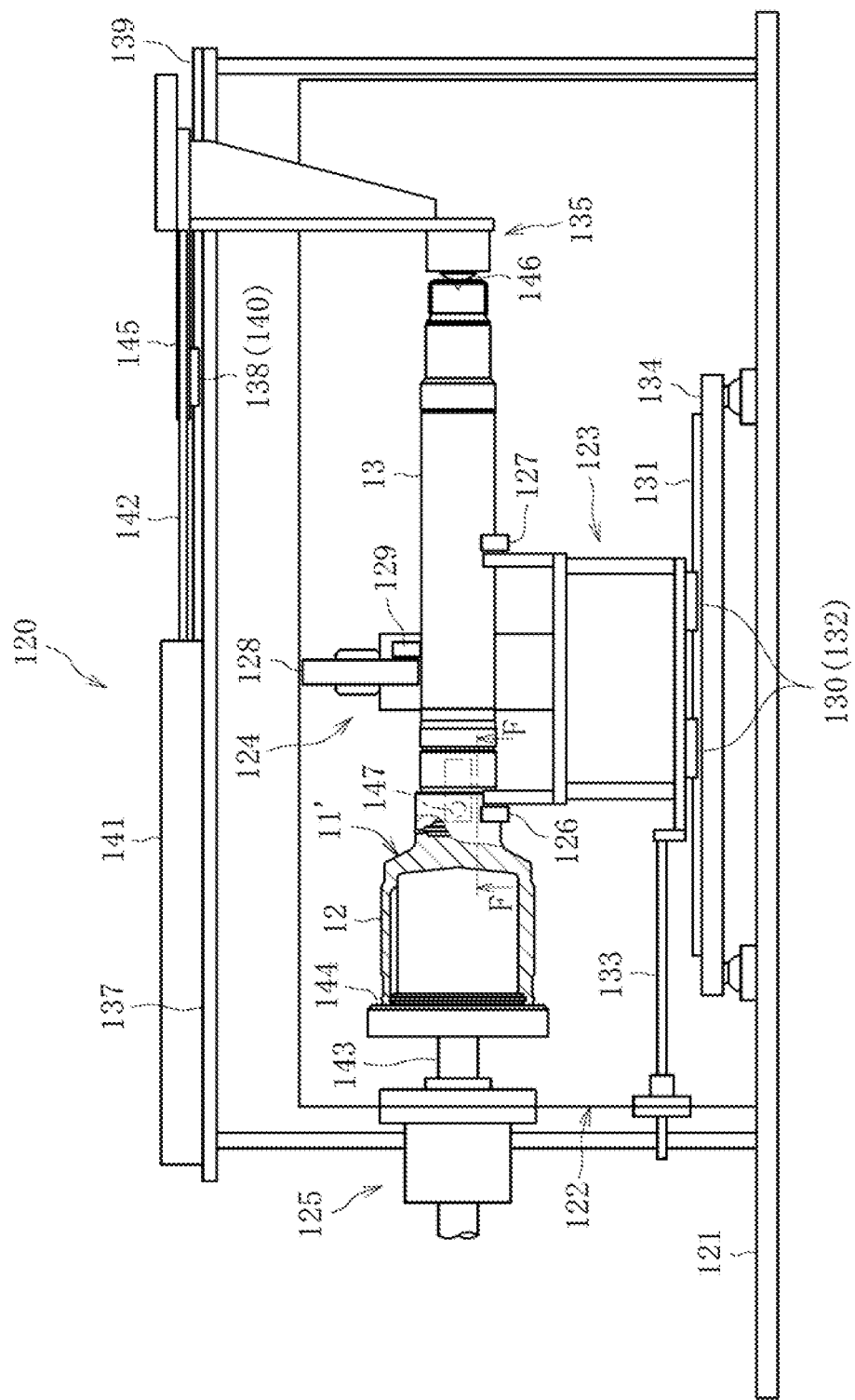
FIG. 10 is a front view for illustrating the overview of the ultrasonic flaw detection-inspection apparatus.
Figure 11:
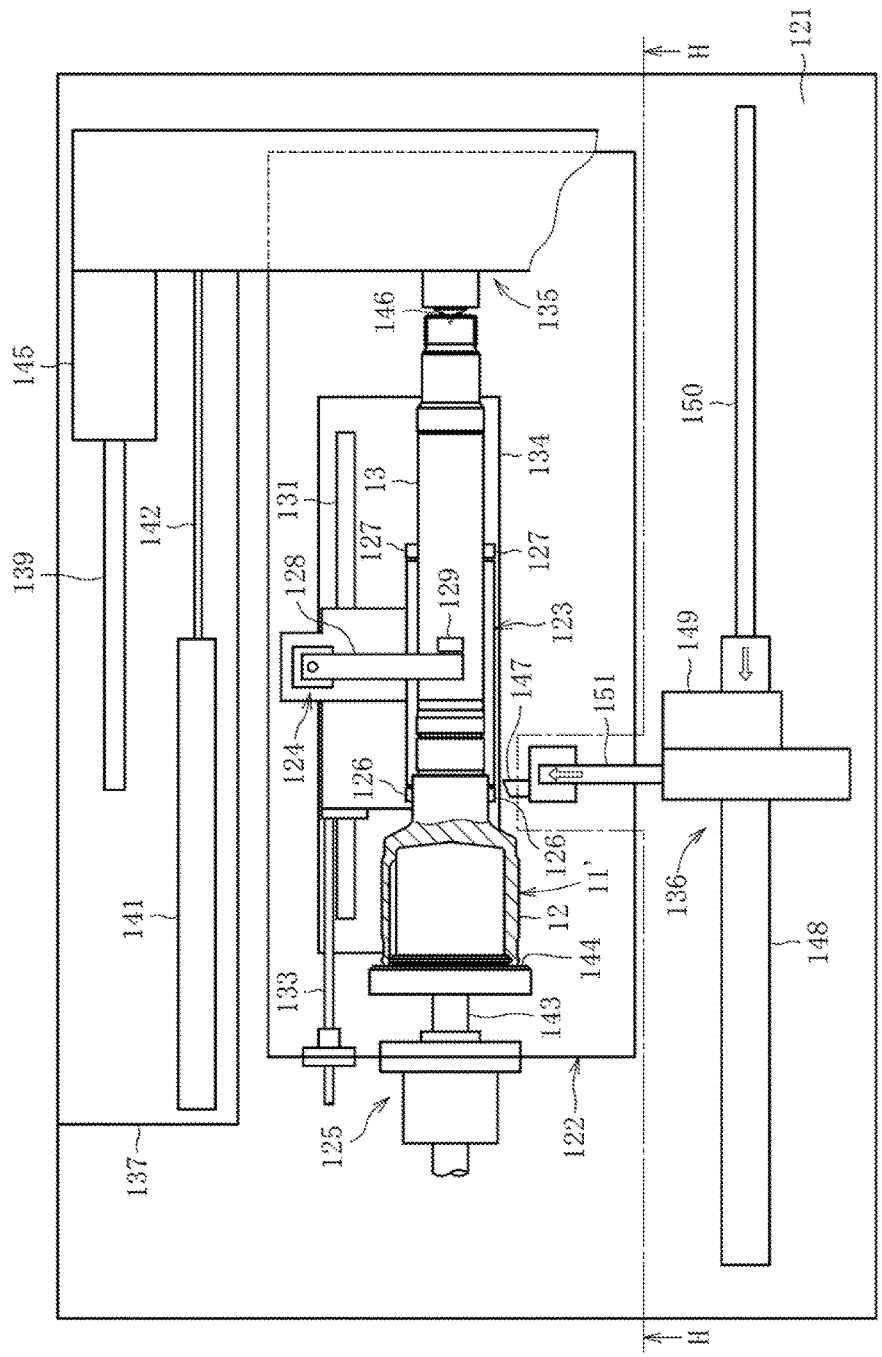
FIG. 11 is a plan view for illustrating the overview of the ultrasonic flaw detection-inspection apparatus.

Following the above description of the overview of the manufacturing steps (processing steps) of this embodiment, the features of this embodiment, that is, the ultrasonic flaw detection-inspection step for the welded portion is described with reference to FIG. 8 to FIG. 13. FIG. 8 is a front view for illustrating an overview of an ultrasonic flaw detection-inspection apparatus as viewed from the arrow G-G of FIG. 9. FIG. 9 is a plan view for illustrating the ultrasonic flaw detection-inspection apparatus. In each of the states illustrated in FIG. 8 and FIG. 9, the outer joint member after welding is placed in the ultrasonic flaw detection-inspection apparatus. FIG. 10 is a front view for illustrating a state during inspection as viewed from the arrow H-H of FIG. 11. FIG. 11 is a plan view for illustrating the state during inspection.

As illustrated in FIG. 8 and FIG. 9, an ultrasonic flaw detection-inspection apparatus 120 mainly comprises a water bath 122 mounted at the center of a base 121, a workpiece support 123, a workpiece holding member 124, a rotary drive device 125 configured to rotate an intermediate product 11' of the outer joint member 11 (hereinafter also referred to as "workpiece 11'"), a pressing device 135 configured to press an axial end of the workpiece 11', and a drive positioning device 136 (see FIG. 9) for a probe.

As illustrated in FIG. 8, the workpiece support 123 comprises rollers 126 and 127 configured to allow the workpiece 11' to be placed thereon in a freely rotatable manner. As illustrated in FIG. 9, the rollers 126 and 127 are arranged in pairs so that the shaft section 13 of the workpiece 11' can be stably supported. The rollers 126 are located at a portion close to the welded portion, and the rollers 127 are located at a center portion of the shaft section 13. The rollers 126 and 127 are capable of adjusting the placement position of the workpiece 11' as appropriate in the axial direction (lateral direction of FIG. 9) and the radial direction (vertical direction of FIG. 9) in consideration of a joint size, dimensions, and weight balance of the workpiece 11'.

Further, the workpiece holding member 124 is mounted to the workpiece support 123 at a position displaced from an axial line of the workpiece 11' in a horizontal direction (see FIG. 9). The workpiece holding member 124 comprises a lever 128, and a workpiece holding roller 129 is arranged at an end portion of the lever 128. The lever 128 is pivotable in the plane, and is vertically movable.

The workpiece support 123 is mounted to a support 134 through intermediation of a linear-motion bearing 130 comprising rails 131 and linear guides 132, and is movable in the axial direction (lateral direction of FIG. 8 and FIG. 9). The support 134 is mounted to the base 121. A rod 1383 is coupled to an end portion (left end portion of FIG. 8 and FIG. 9) of the workpiece support 123 so that the workpiece support 123 is driven to be positioned by an actuator (not shown) on an outside of the water bath 122.

The rotary drive device 125 comprises a rotary shaft 143 having a rotary disc 144 mounted thereto, and this rotary shaft 143 is driven to rotate by a motor (not shown) on the outside of the water bath 122.

As illustrated in FIG. 8, a mounting base 137 is arranged on an upper side of the ultrasonic flaw detection-inspection apparatus 120. A base plate 145 for the pressing device 135 configured to press the axial end of the workpiece 11' is mounted to the mounting base 137 through intermediation of a linear-motion bearing 138 comprising a rail 139 and a linear guide 140 so that the pressing device 135 is movable in the axial direction (lateral direction of FIG. 8 and FIG. 9). A rod 142 of a pneumatic cylinder 141 is coupled to an end portion of the base plate 146 for the pressing device 135 so that the pressing device 135 is driven. A free bearing 146 is mounted to a portion to be held in abutment against the axial end of the shaft section 13 of the workpiece 11' so that the axial end can be pressed in a freely rotatable manner.

As illustrated in FIG. 9, the drive positioning device 136 for a probe is arranged at a position displaced from the axial line of the workpiece 11' in a horizontal direction. This drive positioning device 136 comprises actuators for the X-axis direction (lateral direction of FIG. 9) and the Y-axis direction (vertical direction of FIG. 9) so that a probe 147 is driven to be positioned in the X-axis and Y-axis directions. An actuator 148 for the X-axis direction and an actuator 149 for the Y-axis direction are each an electric ball-screw type (electric cylinder), which is capable of performing positioning with high accuracy. Reference symbol 150 represents a rail for a linear-motion bearing. The drive positioning device 136 is arranged on the outside of the water bath 122, and the probe 147 and a holder 151 therefor are arranged in the water bath 122.

Next, the operation of the ultrasonic flaw detection-inspection apparatus 120 and the ultrasonic flaw detection-inspection step S6k are described. As illustrated in FIG. 8 and FIG. 9, the workpiece 11' after welding is placed on the workpiece support 123 by a loading device (not shown). At this time, in order that the workpiece 11' is loaded, the workpiece support 123 is located at an appropriate interval from the rotary drive device 125 in the axial direction of the workpiece 11', and the workpiece holding member 124 raises and pivots the lever 128 thereof so as to be substantially parallel to the axial line of the workpiece 11'. Further, the pressing device 135 and the drive positioning device 136 for a probe wait at retreated positions.

After that, the lever 128 of the workpiece holding member 124 is pivoted so as to be substantially perpendicular to the axial line of the workpiece 11', and then lowered to hold the workpiece 11' from above (see FIG. 10). Then, water is supplied to the water bath 122. In the ultrasonic flaw detection-inspection apparatus 120 according to this embodiment, flaw detection is performed under water, and hence ultrasonic waves are satisfactorily propagated. Thus, inspection can be performed with high accuracy.

Next, as illustrated in FIG. 10 and FIG. 11, the pneumatic cylinder 141 is driven to cause the pressing device 135 to be advanced and pressed against the axial end of the workpiece 11', thereby pressing the opening rim of the cup section 12 of the workpiece 11' against the rotary disc 144 of the rotary drive device 125. In conjunction with the advance of the pressing device 135, the workpiece support 123 is also moved toward the rotary drive device 125. Thus, the workpiece 11' is positioned in the radial direction and the axial direction. In this state, the motor (not shown) of the rotary drive device 125 is rotated, thereby rotating the workpiece 11'.

As illustrated in FIG. 11, the drive positioning device 136 is moved in the X-axis direction, and then moved in the Y-axis direction, thereby positioning the probe 147 at a flaw detection position (in FIG. 10, the probe 147 in this state is indicated by the broken line). Then, the flaw-detection inspection is performed. After the flaw-detection inspection, the water is drained, and the workpiece 11' is unloaded from the ultrasonic flaw detection-inspection apparatus 120 by the loading device (not shown). As described above, the inspection is sequentially repeated on the workpieces 11'.

In the ultrasonic flaw detection-inspection apparatus 120 according to this embodiment, in order to reduce the cycle time of the inspection, time-consuming supply and drainage of water are performed simultaneously with the operations of the devices and the members, or at other timings in accordance therewith. Further, some of the operations of the devices and the members may be performed simultaneously with each other or in different orders as appropriate.

Figure 12A:
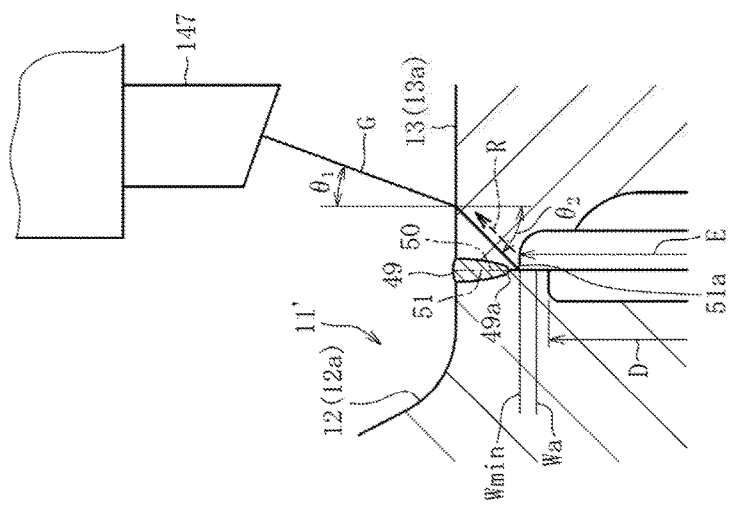
FIG. 12a is a partial enlarged view as viewed from the arrow F-F of FIG. 10, for illustrating a case of a non-defective welded product.
Figure 12B:
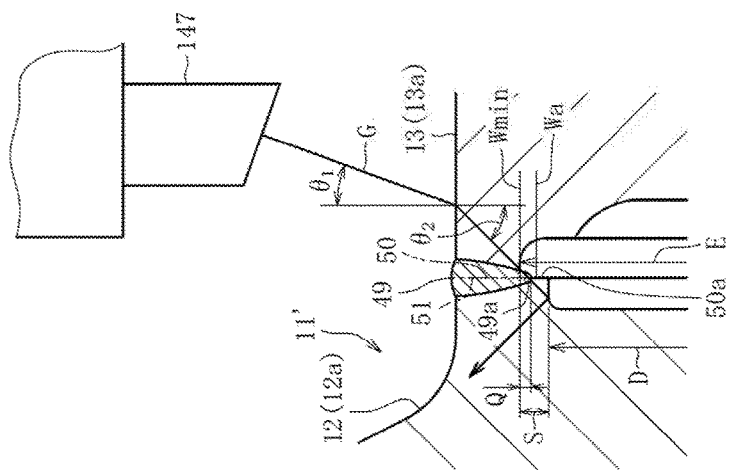
FIG. 12b is a partial enlarged view as viewed from the arrow F-F of FIG. 10, for illustrating a defective welded product.
Figure 13:
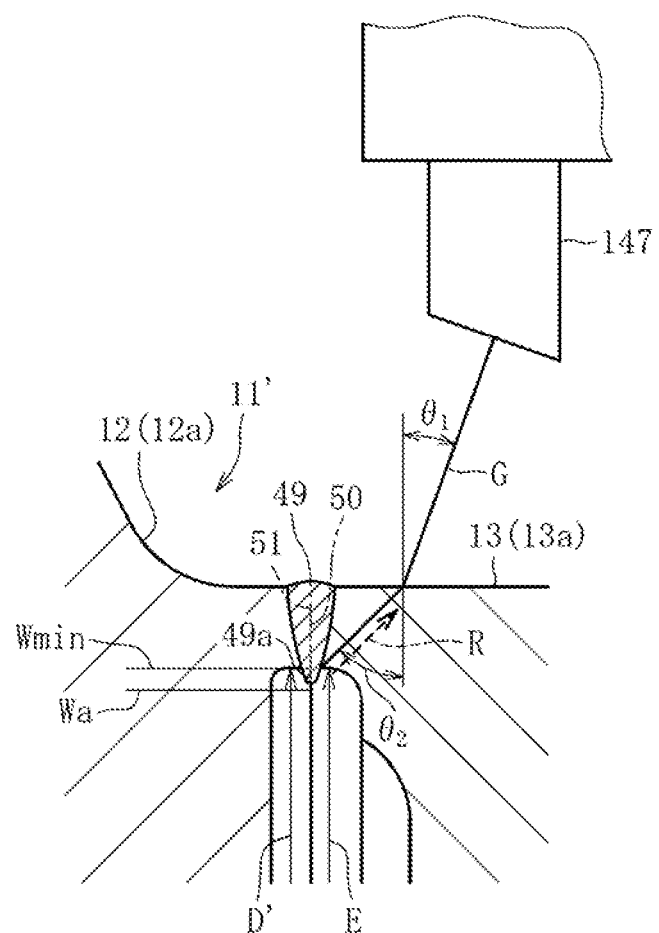
FIG. 13 is a view for illustrating findings in the course of development.

Details of the ultrasonic flaw-detection inspection are described with reference to FIG. 12a, FIG. 12b, and FIG. 13. All of FIG. 12a, FIG. 12b, and FIG. 13 are views as viewed from the arrow F-F of FIG. 10. FIG. 12a is an illustration of a non-defective welded product, and FIG. 12b is an illustration of a defective welded product. FIG. 13 is an illustration of findings in the course of development.

The probe 147 is positioned at the flaw detection position away from the welded portion 49 by a predetermined distance. The flaw detection position is preset for each joint size. A target welding depth is denoted by the reference symbol Wa, and a minimum acceptable welding depth is denoted by the reference symbol Wmin. Workpieces having a depth equal to or larger than the minimum acceptable welding depth Wmin are determined as non-defective welded products, and workpieces having a depth smaller than the minimum acceptable welding depth Wmin are determined as defective welded products. When a transmission pulse G is transmitted at an incident angle θ1 from the probe 147, the transmission pulse G is refracted by the surface of the shaft section 13, and advances at a refraction angle θ2. The ultrasonic flaw-detection inspection of this embodiment is performed under the condition that the incident angle θ1 is approximately 20°, and the refraction angle θ2 is approximately 45°. During the flaw-detection inspection, the workpiece 11' is kept rotated by the rotary drive device 125 (see FIG. 10).

The probe 147 positioned at the flaw detection position away from the welded portion 49 by the predetermined distance collects data of the entire periphery of the workpiece 11'. Specifically, in consideration of tolerance for displacement of the welding position, at the above-mentioned flaw detection position, first, data of a single rotation (360°) of the workpiece 11' is collected. Then, the probe 147 is sequentially shifted in the axial direction at a minute pitch (for example, 0.5 mm) to collect data of a plurality of rotations (for example, five rotations). Based on those pieces of data, non-defective/defective determination is made. A threshold of a reflected echo to be used in the non-defective/ defective determination is determined based on a welding pattern corresponding to the minimum acceptable welding depth Wmin.

Advantages in the ultrasonic flow-detection inspection to be obtained by the shape of the welded portion of the cup member 12a and the shaft member 13a are described. As described above, the inner diameter D of the joining end surface 50 of the cup member 12a is set smaller than the inner diameter E of the joining end surface 51 of the shaft member 13a. On the joining end surface 50 of the cup member 12a, the protruding surface 50a protruding to the radially inner side with respect to the inner diameter E of the joining end surface 51 of the shaft member 13a is formed. In such a state, the cup member 12a and the shaft member 13a are welded to each other.

Details of the advantages to be obtained by the shape of the above-mentioned welded portion are described by way of an example of cases of the non-defective welded product and the defective welded product. In the case of the non-defective welded product, when the transmission pulse G from the probe 147 is input as illustrated in FIG. 12a, the transmission pulse G enters the cup section 12 through a back bead 49a at the depth equal to or larger than the minimum acceptable welding depth Wmin, and travels straight as it is. Alternatively, the transmission pulse G is transmitted to the cup section 12 side by being reflected due to the inner diameter D of the cup section 12. In those cases, the probe 147 does not receive a reflected echo. This is because, as described above, on the joining end surface 50 of the cup member 12a, the protruding surface 50a protruding to the radially inner side with respect to the inner diameter E of the joining end surface 51 of the shaft member 13a is formed. Thus, even when the transmission pulse G enters the back bead 49a, the boundary surface of the back bead 49a, which is perpendicular to the transmission pulse G, does not exist. For this reason, although a slightly-scattered reflected echo is generated, the reflected echo does not have such an intensity as to cause a detection error of the probe 147. Thus, the intensity of the reflected echo received by the probe 147 is equal to or less than the threshold, and hence determination that the welded product is non-defective is made. As described above, when the protruding surface 50a is formed on the joining end surface 50 of the cup member 12a, the intensity of the reflected echo is reduced. Thus, the accuracy in the inspection can be enhanced.

The findings in the course of the development to arrive at the shape of the welded portion of this embodiment are illustrated in FIG. 13. In this case, an inner diameter D' of the joining end surface 50 of the cup member 12a is set to an equal dimension to the inner diameter E of the joining end surface 51 of the shaft member 13a. In this non-defective welded product, which has a welding depth equal to or larger than the minimum acceptable welding depth Wmin, when the transmission pulse G from the probe 147 is input, due to the boundary surface of the back bead 49a, which is perpendicular to the transmission pulse G, a reflected echo R reflected by this boundary surface is received by the probe 147. Although reflected echoes from the back bead 49a are scattered, the reflected echo R is strong to have such an intensity as to be more than the threshold of the reflected echo for the non-defective/defective determination. Thus, determination that the welded product is defective is made. For this reason, it was proved that the determination as to whether the welded product was non-defective or defective was difficult. Based on those findings, the inventors of the present invention arrived at the shape of the welded portion of this embodiment.

Next, a case of a defective welded product is described. As illustrated in FIG. 12b, when the transmission pulse G from the probe 147 is input under a state in which a distal end of the back bead 49a does not reach the minimum acceptable welding depth Wmin, the transmission pulse G is reflected by the joining end surface 51 and a chamfered portion 61a, and the scattered reflected echo R is received by the probe 147. The intensity of the reflected echo R is more than the threshold of the reflected echo for the non-defective/defective determination, and hence determination that the welded product is defective is made. As described above, the protruding surface 50a is formed on the joining end surface 50, and hence the intensities of the reflected echoes can be clearly discriminated from each other. Thus, the determination as to whether the welded product is non-defective or defective can be made with high accuracy.

Dimensions of the protruding surface 50a are set so that a relationship of S≥Q is established, where S[S=(E−D)/2] is a width of the protruding surface 50a in a radial direction, and where Q is a height of the back bead 49a from the inner diameter E of the joining end surface 51 as illustrated in FIG. 12a. When this relationship is satisfied, the intensities of the reflected echoes can be clearly discriminated from each other. Thus, the determination as to whether the welded product is non-defective or defective can be made with high accuracy. As long as the relationship of S≥Q is maintained, the dimensions of the protruding surface 50a may be changed as appropriate.

As described above, the ultrasonic flaw detection-inspection apparatus 120 according to this embodiment mainly comprises the water bath 122 mounted at the center of the base 121. In the water bath 122, the workpiece support 123, the workpiece holding member 124, the rotary disc 144 of the rotary drive device 126 configured to rotate the workpiece 11', the free bearing 146 of the pressing device 136 configured to press the axial end of the workpiece 11', and the probe 147 mounted to the drive positioning device 136 are arranged. With this configuration, the operation of loading the workpiece 11', the supply and drainage of water, the flaw-detection inspection, and the operation of unloading the workpiece 11' can be performed in conjunction with each other, and the ultrasonic flaw-detection inspection can be automated. Thus, accuracy, operability, and efficiency in the inspection can be enhanced, which is suited to the inspection on the welded portion of the outer joint member of the constant velocity universal joint being a mass-produced product.

Further, the outer diameter B of the joining end surface 60 of the cup member 12a of this embodiment is set to an equal dimension for each joint size. Also with this base configuration, in the ultrasonic flaw-detection inspection, setup operations with respect to the outer joint members 11 having the different product numbers are simplified. Thus, the efficiency in the inspection can be further enhanced.

Still further, flaw detection is performed under water, and hence ultrasonic waves are satisfactorily propagated. Thus, inspection can be performed with much higher accuracy. In addition, through employment of the shape of the welded portion, in which the protruding surface 50a is formed on the joining end surface 50, the intensities of the reflected echoes can clearly be discriminated from each other. Thus, the determination as to whether the welded product is non-defective or defective can be made with high accuracy.

Figure 14:
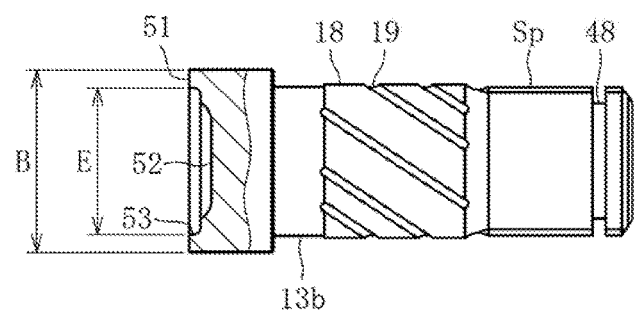
FIG. 14 is a front view for illustrating a shaft member assigned with a different product number.
Figure 15:
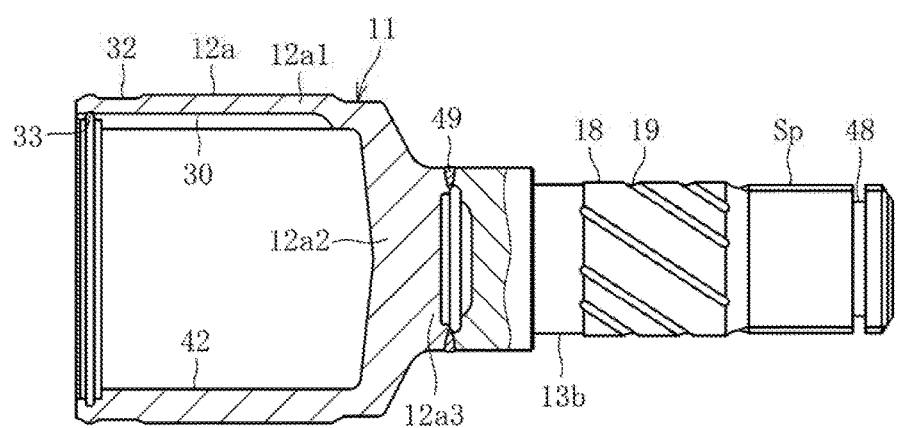
FIG. 15 is a partial vertical sectional view for illustrating an outer joint member that is manufactured using the shaft member illustrated in FIG. 14.

To summarize the manufacturing concept, standardization of a product type of the cup member is additionally described while exemplifying a shaft member having a product number different from that of the above-mentioned shaft member 13a of the long stem type illustrated in FIG. 5. A shaft member 13b illustrated in FIG. 14 and FIG. 15 is used as a general stem type on the inboard side. The shaft member 13b has the joining end surface 51 to be brought into abutment against the joining end surface 50 (see FIG. 4b) of the bottom portion 12a2 (projecting portion 12a3) of the cup member 12a. The outer diameter B and the inner diameter E of the joining end surface 51 are set to the equal dimensions to the outer diameter B and the inner diameter E of the joining end surface 51 of the shaft member 13a of the long stem type illustrated in FIG. 5. Also in this case, the inner diameter D of the joining end surface 50 of the cup member 12a is set smaller than the inner diameter E of the joining end surface 51 of the shaft member 13b. On the joining end surface 50 of the cup member 12a, the protruding surface 50a protruding to the radially inner side with respect to the inner diameter E of the joining end surface 51 of the shaft member 13b is formed. In such a state, the cup member 12a and the shaft member 13b are welded to each other.

The shaft member 13b is used as the general stem type on the inboard side. Accordingly, the shaft member 13b comprises a shaft section with a small length, and a sliding bearing surface 18 formed on an axial center portion thereof, and a plurality of oil grooves 19 are formed in the sliding bearing surface 18. The spline Sp and a snap ring groove 48 are formed in an end portion of the shaft member 13b on the side opposite to the cup member 12a side. As described above, even when there are differences in types, such as the general length stem type and the long stem type, and shaft diameters and outer peripheral shapes vary in each vehicle type, the diameter B of the joining end surface 51 of the shaft member 13a or 13b is set to an equal dimension.

The outer diameter B of the joining end surface 50 of the cup member 12a and the joining end surface 51 of the shaft member 13a or 13b is set to an equal dimension for each joint size. Thus, the cup member prepared for common use for each joint size, and the shaft member having a variety of specifications of the shaft section for each vehicle type can be prepared in a state before heat treatment. Further, the intermediate component of each of the cup member 12a and the shaft member 13a or 13b can be assigned with a product number for management. When standardizing product types of the cup member 12a, various types of the outer joint members 11 satisfying requirements can be produced quickly through combination of the cup member 12a and the shaft member 13a or 13b having a variety of specifications of the shaft section for each vehicle type. Therefore, standardization of a product type of the cup member 12a can reduce cost and alleviate a burden of production management.

The standardization of the product type of the cup member is described above by taking the differences in types, such as the general length stem type and the long stem type, as an example for easy understanding, but the present invention is not limited thereto. The same applies to standardization of the product type of the cup member for shaft members having a variety of specifications of the shaft section for each vehicle type among the general length stem types, and for shaft members having a variety of specifications of the shaft section for each vehicle type among the long stem types.

Figure 16:
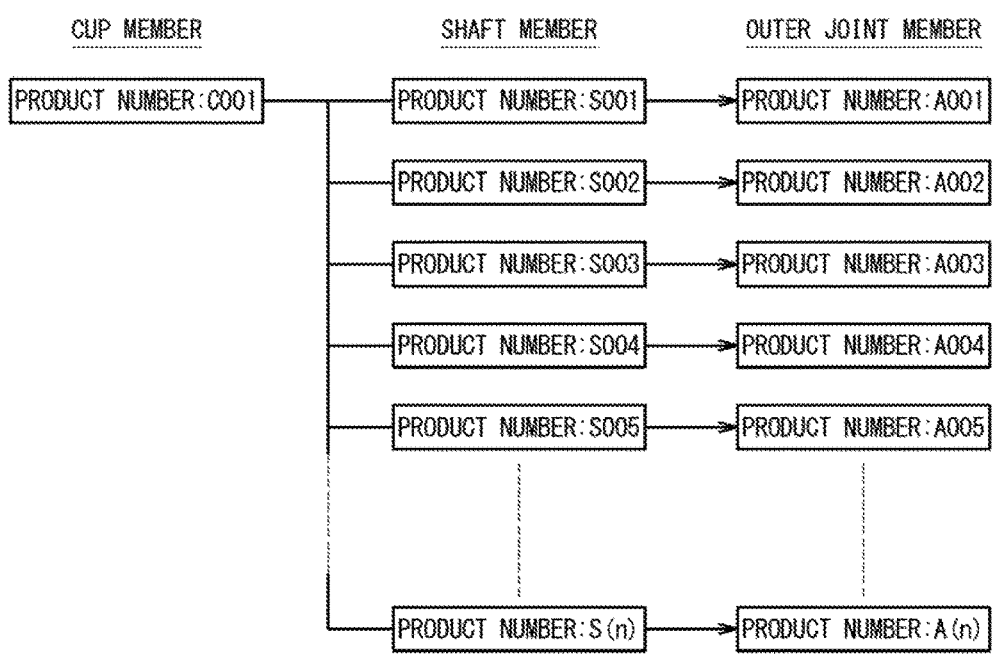
FIG. 16 is a diagram for illustrating an example of standardization of a product type of the cup member.

As a summary of the above description, FIG. 16 is a diagram for illustrating an example of standardization of a product type of the cup member according to this embodiment. As illustrated in FIG. 16, the cup member is prepared for common use for one joint size, and is assigned with, for example, a product number C001 for management. In contrast, the shaft member has a variety of specifications of the shaft section for each vehicle type, and is assigned with, for example, a product number S001, S002, or S(n) for management. For example, when the cup member assigned with the product number C001 and the shaft member assigned with the product number S001 are combined and welded to each other, the outer joint member assigned with a product number A001 can be produced. Thus, owing to standardization of a product type of the cup member, it is possible to reduce cost and to alleviate a burden of production management. In the standardization of a product type, the cup member is not limited to one type for one joint size, that is, not limited to one type assigned with a single product number. For example, the cup member comprises cup members of a plurality of types (assigned with a plurality of product numbers, respectively) that are prepared for one joint size based on different specifications of a maximum operating angle, and are each prepared so that the outer diameter B of the joining end surface of each of those cup members has an equal dimension.

Figure 17:
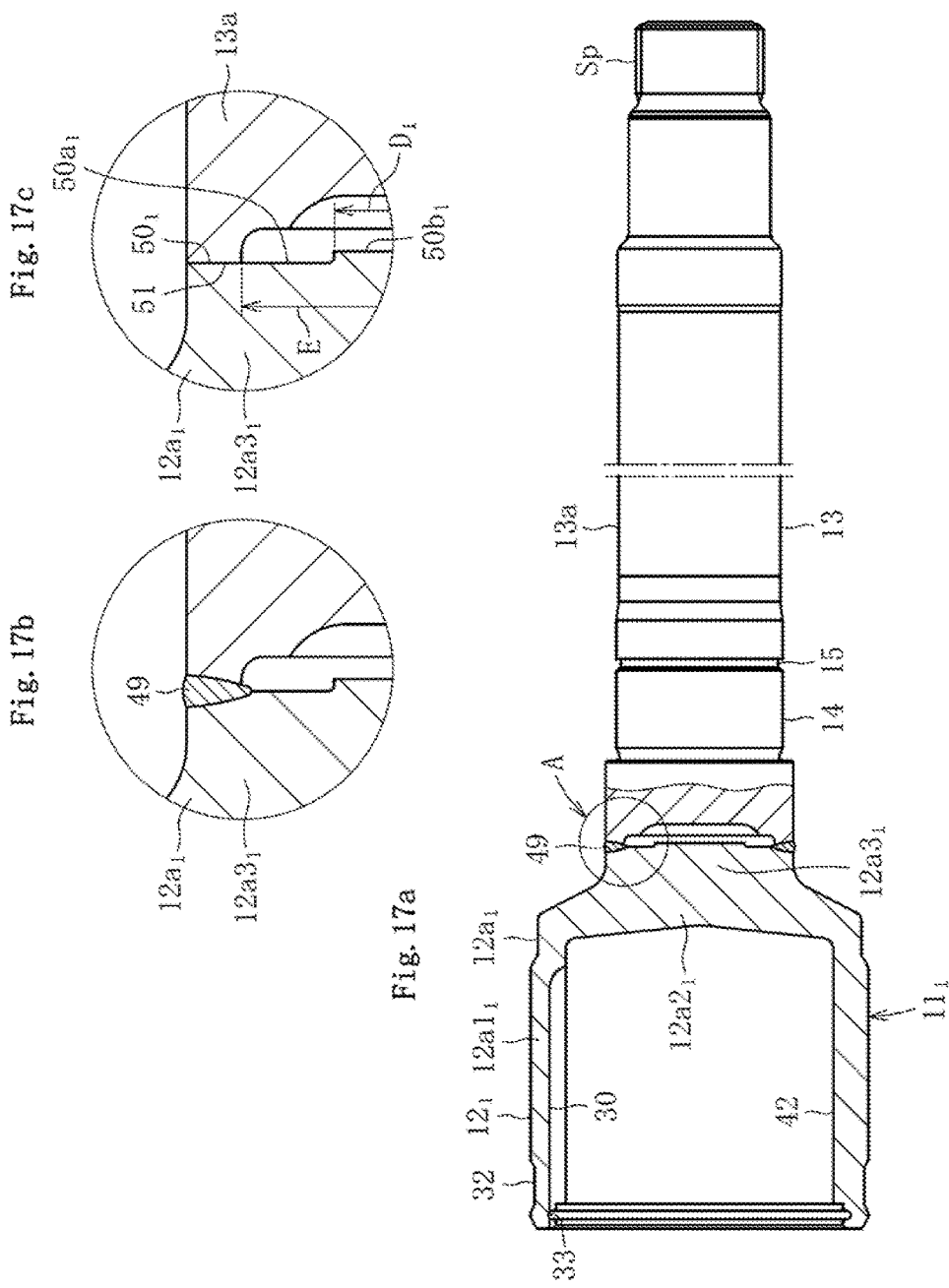
Figure 18:
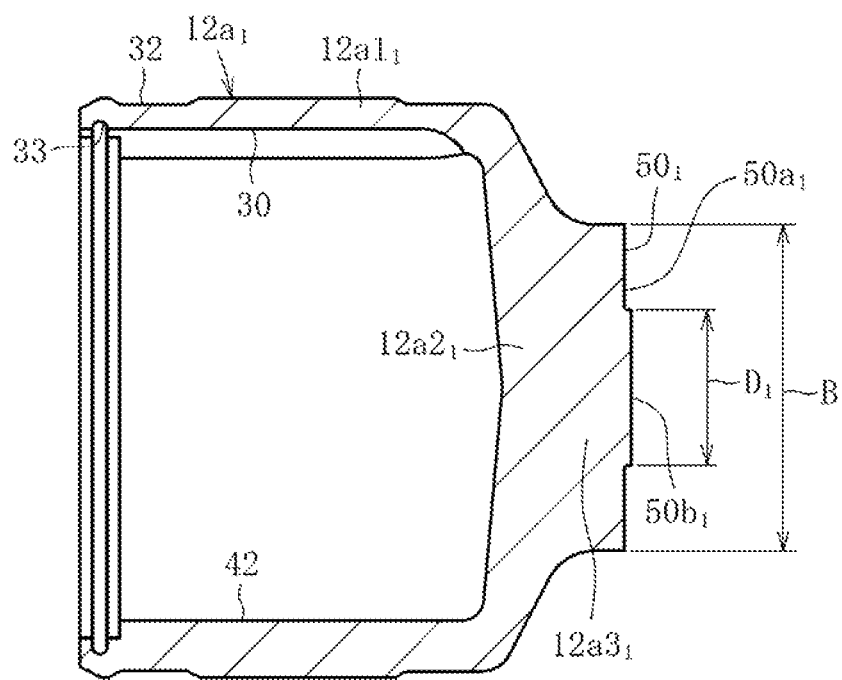
FIG. 18 is a vertical sectional view for illustrating the entirety of a cup member of FIG. 17c.

A modification of the outer joint member according to the first embodiment is described with reference to FIG. 17 and FIG. 18. FIG. 17a is a partial vertical sectional view for illustrating an outer joint member of this modification, FIG. 17b is an enlarged view for illustrating a circle "A" of FIG. 17a, and FIG. 17c is a view for illustrating a state before welding in FIG. 17b. FIG. 18 is a vertical sectional view for illustrating the entirety of a cup member before welding. A form of a protruding surface formed on a joining end surface of the cup member of this modification is different from that in the first embodiment, and other features are the same as those in the first embodiment. Thus, parts that have the same function are denoted by the same reference symbols (except for the subscripts), and only main points are described.

As illustrated in FIG. 17c and FIG. 18, a joining end surface $50_1$ formed on a projecting portion $12_1a3$ of a bottom portion $12_1a2$ of a cup member $12_1a$ is formed by annular turning. In this case, a diameter $D_1$ of the joining end surface $50_1$ on the radially inner side corresponds to the inner diameter D of the joining end surface 50 of the cup member 12a of the first embodiment. Thus, as illustrated in FIG. 17c, a portion on the radially inner side with respect to the inner diameter E of the shaft member 13a corresponds to a protruding surface $50_1a$. The cup member $12_1a$ of this modification can be formed by turning an end surface of the projecting portion 12a3' of the preform 12a' for the above-mentioned cup member after ironing, which is illustrated in FIG. 4a, at only a portion corresponding to the joining end surface $50_1$ on the radially outer side as illustrated in FIG. 18. Thus, the time for the turning can be reduced. Note that, the present invention is not limited thereto, and a projecting surface portion $50b_1$ of the joining end surface on the radially inner side of FIG. 18 may be subjected to turning.

Other features and advantages, that is, details of the overview of the respective steps, the states of the cup member and the shaft member in the main processing steps, the preparation of the cup member for common use, the welding method, the ultrasonic flaw detection-inspection method, the standardization of the product type, the configuration of the outer joint member, and the like as described above in the first embodiment on the manufacturing method are the same as those of the first embodiment. Therefore, all the details of the first embodiment are applied in this embodiment to omit redundant description.

Figure 19:
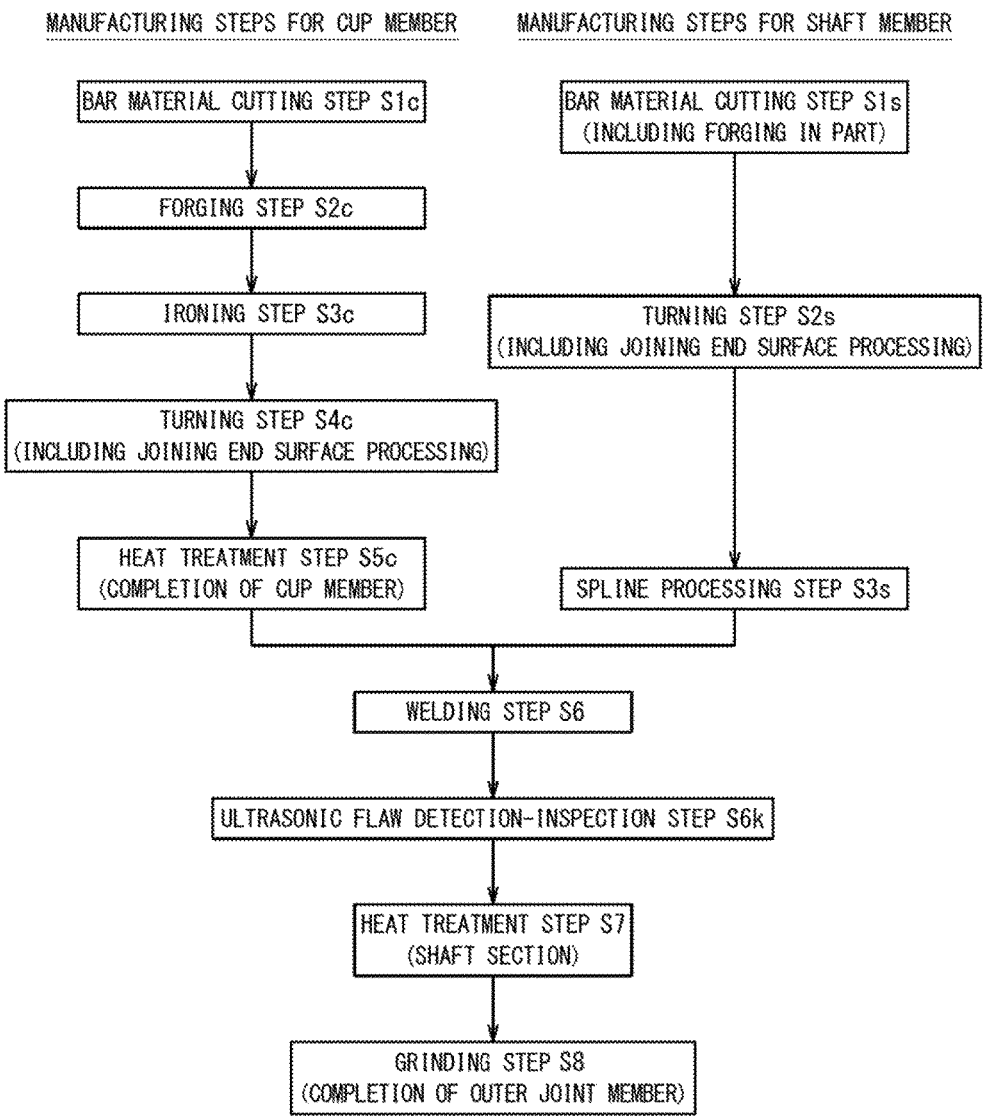
FIG. 19 is a diagram for illustrating an overview of a method of manufacturing an outer joint member according to a second embodiment of the present invention.

FIG. 19 is an illustration of a manufacturing method according to a second embodiment of the present invention. In the manufacturing steps of this embodiment, the heat treatment step for the cup member, which is involved in the heat treatment step S7 in FIG. 3 as described above in the first embodiment, is provided before the welding step S6 in the sequence and named "heat treatment step S5c", to thereby prepare the cup member as a finished product. Details of other aspects of the second embodiment than this aspect, that is, details of the overview of the respective steps, the states of the cup member and the shaft member in the main processing steps, the preparation of the cup member for common use, the welding method, the ultrasonic flaw detection-inspection method, the standardization of the product type, the configuration of the outer joint member, and the like as described above in the first embodiment on the manufacturing method are the same as those of the first embodiment. Therefore, all the details of the first embodiment are applied in this embodiment, and only the difference is described.

As illustrated in FIG. 4b, the cup member 12a has a shape extending from the joining end surface 50 to the large-diameter cylindrical portion 12a1 via the bottom portion 12a2, and the portions to be subjected to heat treatment that involves quenching and tempering are the track grooves 30 and the cylindrical inner peripheral surface 42 located at the inner periphery of the cylindrical portion 12a1. Therefore, the cup member 12a generally has no risk of thermal effect on the heat-treated portion during the welding. For this reason, the cup member 12a is subjected to heat treatment before the welding to be prepared as a finished component. The manufacturing steps of this embodiment are suitable in practical use.

In the manufacturing steps of this embodiment, the cup member 12a is subjected to heat treatment for preparing the cup member 12a as a finished product, and is therefore assigned with a product number indicating a finished product for management. Thus, the standardization of the product type of the cup member 12a remarkably reduces the cost and alleviates the burden of production management. Further, the cup member 12a can be manufactured solely until the cup member 12a is completed as a finished product through the forging, turning, and heat treatment. Thus, the productivity is enhanced by virtue of reduction of setups and the like as well.

In this embodiment, in FIG. 16 for illustrating the example of standardization of the product type of the cup member as described above in the first embodiment, only the product number of the cup member in FIG. 16 is changed to the product number indicating a finished product, whereas the product numbers of the shaft member and the outer joint member are the same as those of the first embodiment. Therefore, description thereof is omitted herein.

Figure 20:
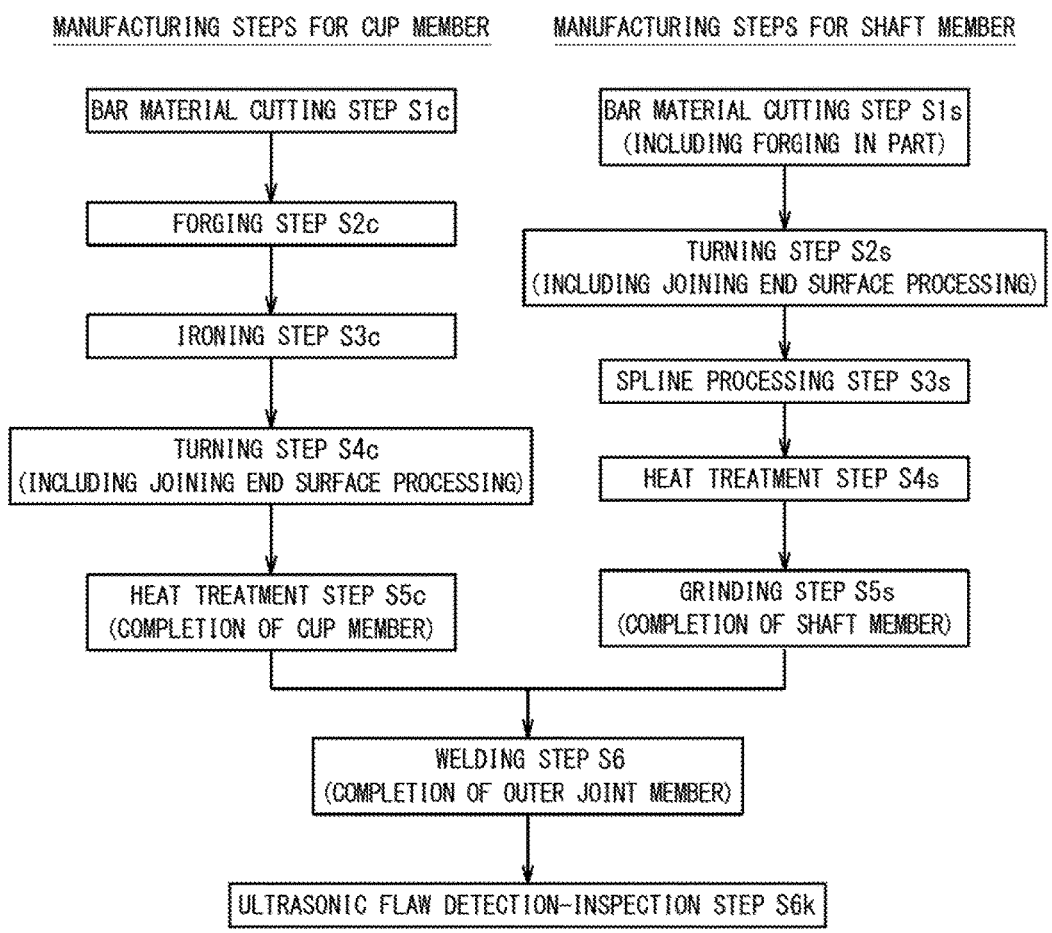
FIG. 20 is a diagram for illustrating an overview of a method of manufacturing an outer joint member according to a third embodiment of the present invention.

FIG. 20 is an illustration of a manufacturing method according to a third embodiment of the present invention. In the manufacturing steps of this embodiment, the heat treatment steps for the cup section and the shaft section, which are involved in the heat treatment step S7 in FIG. 3 as described above in the first embodiment, and the grinding step S8 for the shaft section in FIG. 3 are provided before the welding step S6 in the sequence and named "heat treatment step S5c for cup member", "heat treatment step S4s for shaft member", and "grinding step S5s". Thus, both the cup member and the shaft member are prepared as finished products. Details of other aspects of the third embodiment than this aspect, that is, details of the overview of the respective steps, the states of the cup member and the shaft member in the main processing steps, the preparation of the cup member for common use, the welding method, the ultrasonic flaw detection-inspection method, the standardization of the product type, the configuration of the outer joint member, and the like as described above in the first embodiment on the manufacturing method are the same as those of the first embodiment. Therefore, all the details of the first embodiment are applied in this embodiment, and only the difference is described.

After the spline processing step S3s, a hardened layer having a hardness of approximately from 50 HRC to 62 HRC is formed in a predetermined range of the outer peripheral surface of the shaft member by induction quenching in the heat treatment step S4s. Heat treatment is not performed on a predetermined portion in the axial direction, which includes the joining end surface 51. The heat treatment for the cup member, the assignment of the product number, and the like are the same as those of the second embodiment on the manufacturing method, and redundant description is therefore omitted herein.

After the heat treatment step S4s, the shaft member is transferred to the grinding step S6s so that the bearing mounting surface 14 and the like are finished. Thus, the shaft member is obtained as a finished product. Then, the shaft member is assigned with a product number indicating a finished product for management. The manufacturing steps of this embodiment are suitable in a case of a cup member and a shaft member having shapes and specifications with no risk of thermal effect on the heat-treated portion during the welding.

In the manufacturing steps of this embodiment, both the cup member and the shaft member can be assigned with product numbers indicating finished products for management. Thus, the standardization of the product type of the cup member further remarkably reduces the cost and alleviates the burden of production management. Further, the cup member and the shaft member can be manufactured independently of each other until the cup member and the shaft member are completed as finished products through the forging, turning, heat treatment, grinding after heat treatment, and the like. Thus, the productivity is further enhanced by virtue of reduction of setups and the like as well.

In this embodiment, in FIG. 16 for illustrating the example of standardization of the product type of the cup member as described above in the first embodiment, the product numbers of the cup member and the shaft member in FIG. 16 are changed to the product numbers indicating finished products. The product number of the outer joint member is the same as that of the first embodiment. Therefore, description thereof is omitted herein. Note that, the cup member and the shaft member to be prepared as finished components are not limited to the cup member and the shaft member subjected to finishing such as the above-mentioned grinding after heat treatment or cutting after quenching, but encompass a cup member and a shaft member in a state in which the heat treatment is completed while the finishing is uncompleted.

As described in the standardization of the product type, the cup member is not limited to one type for one joint size, that is, not limited to one type assigned with a single product number. Specifically, as described above, the cup member encompasses, for example, cup members of a plurality of types (assigned with a plurality of product numbers, respectively) that are prepared for one joint size based on different specifications of a maximum operating angle, and are also prepared so that the outer diameters B of the above-mentioned joining end surfaces of the cup members are set to equal dimensions. In addition, the cup member encompasses, for example, cup members of a plurality of types (assigned with a plurality of product numbers, respectively) that are prepared for one joint size in order to achieve management of the cup members in a plurality of forms including intermediate components before heat treatment and finished components in consideration of the joint function, the circumstances at the manufacturing site, the productivity, and the like, and are also prepared so that the outer diameters B of the above-mentioned joining end surfaces of the cup members are set to equal dimensions.

Next, an outer joint member according to a second embodiment of the present invention is described with reference to FIG. 21 and FIG. 22. In this embodiment, parts that have the same function as those of the outer joint member according to the first embodiment are denoted by the same reference symbols, and only main points are described.

Figure 21:
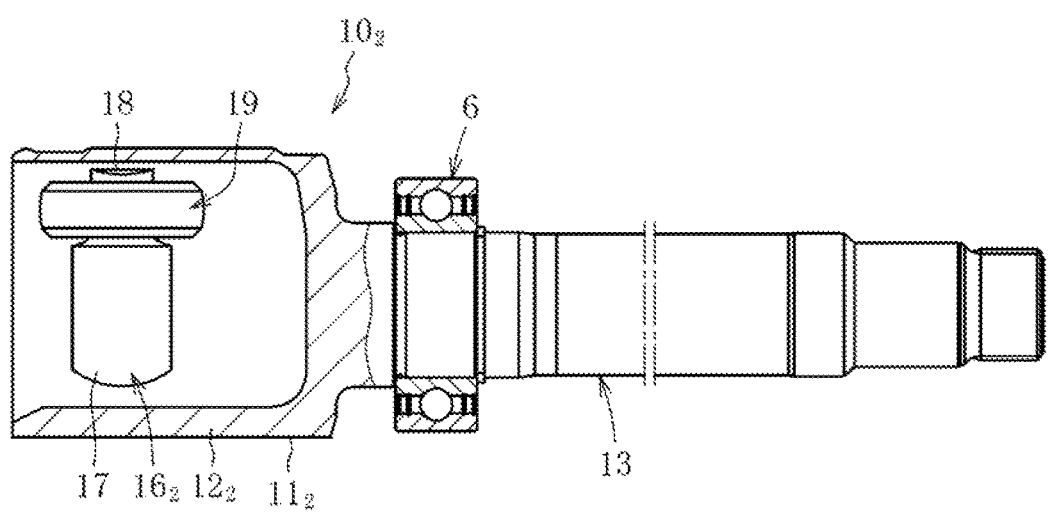
FIG. 21 is a partial vertical sectional view for illustrating a constant velocity universal joint using an outer joint member according to the second embodiment of the present invention.

A plunging type constant velocity universal joint 102 illustrated in FIG. 21 is a tripod type constant velocity universal joint (TJ), and comprises an outer joint member $11_2$ comprising a cup section $12_2$ and the long stem section 13 that extends from a bottom portion of the cup section $12_2$ in the axial direction, an inner joint member $16_2$ housed along an inner periphery of the cup section $12_2$ of the outer joint member $11_2$, and rollers 19 serving as torque transmitting elements that are arranged between the outer joint member $11_2$ and the inner joint member $16_2$. The inner joint member $16_2$ comprises a tripod member 17 comprising three equiangular leg shafts 18 on which the rollers 19 are externally fitted.

Similarly to the outer joint member according to the first embodiment, the inner ring of the support bearing 6 is fixed to the outer peripheral surface of the long stem section 13, and the outer ring of the support bearing 6 is fixed to the transmission case with the bracket (not shown). The outer joint member $11_2$ is supported by the support bearing 6 in a freely rotatable manner, and thus the vibration of the outer joint member $11_2$ during driving or the like is prevented as much as possible.

Figure 22:
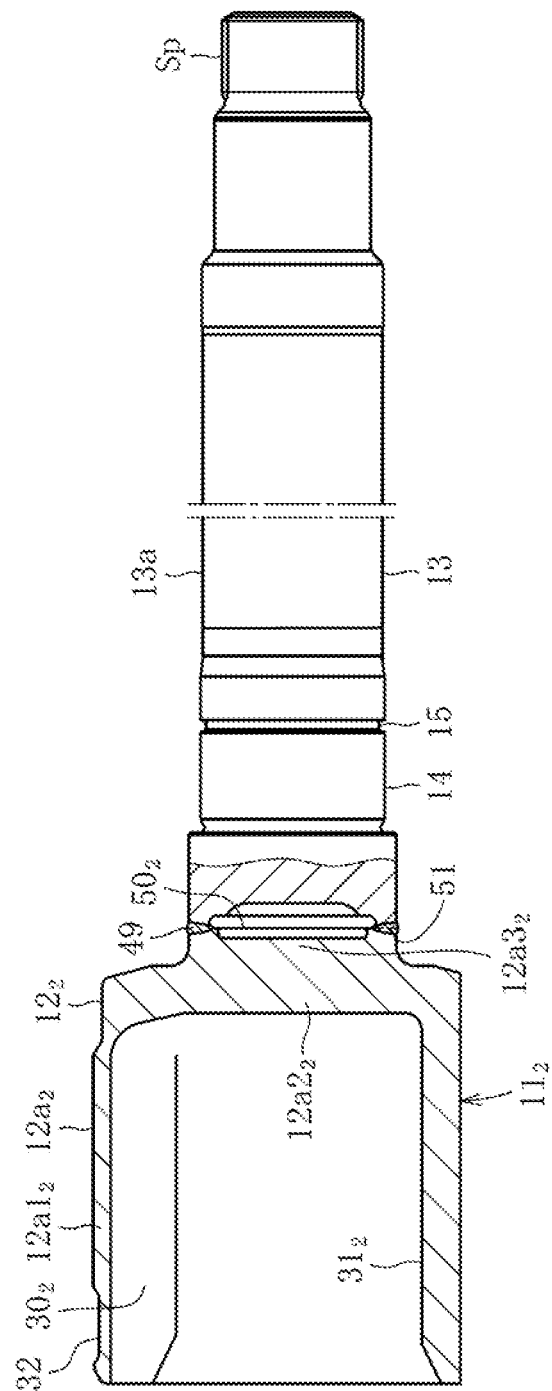
FIG. 22 is a partial vertical sectional view for illustrating the outer joint member of FIG. 21.
Figure 23:
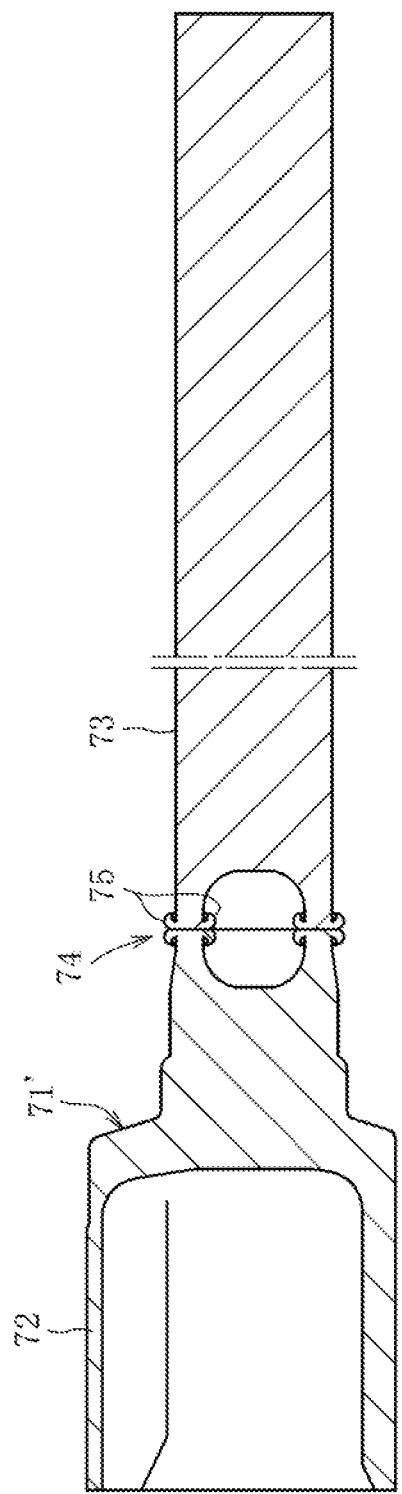
FIG. 23 is a vertical sectional view for illustrating an outer joint member according to a related art.
Figure 24:
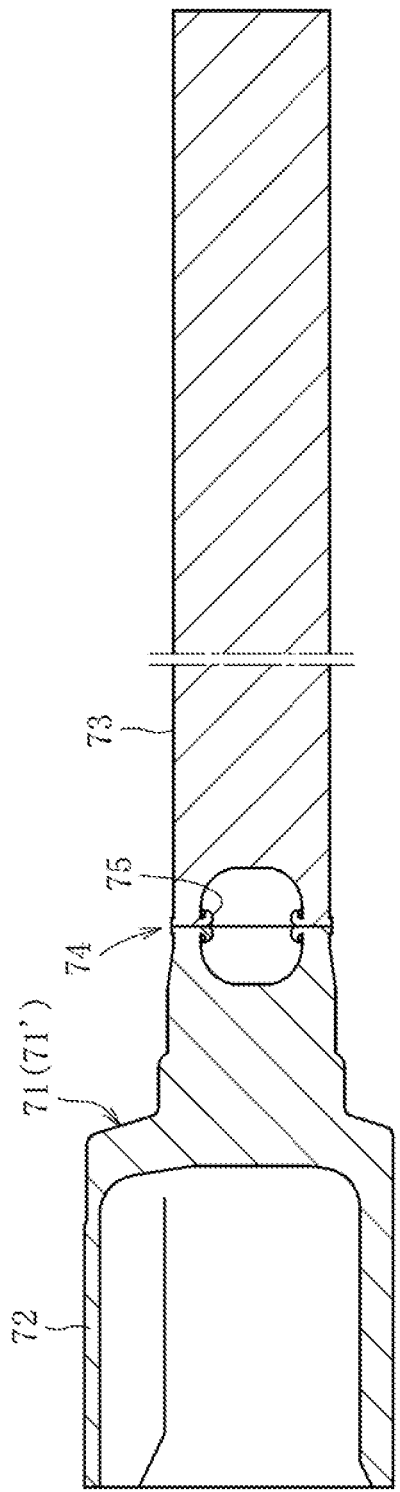
FIG. 24 is a vertical sectional view for illustrating the outer joint member according to the related art.
Figure 25:
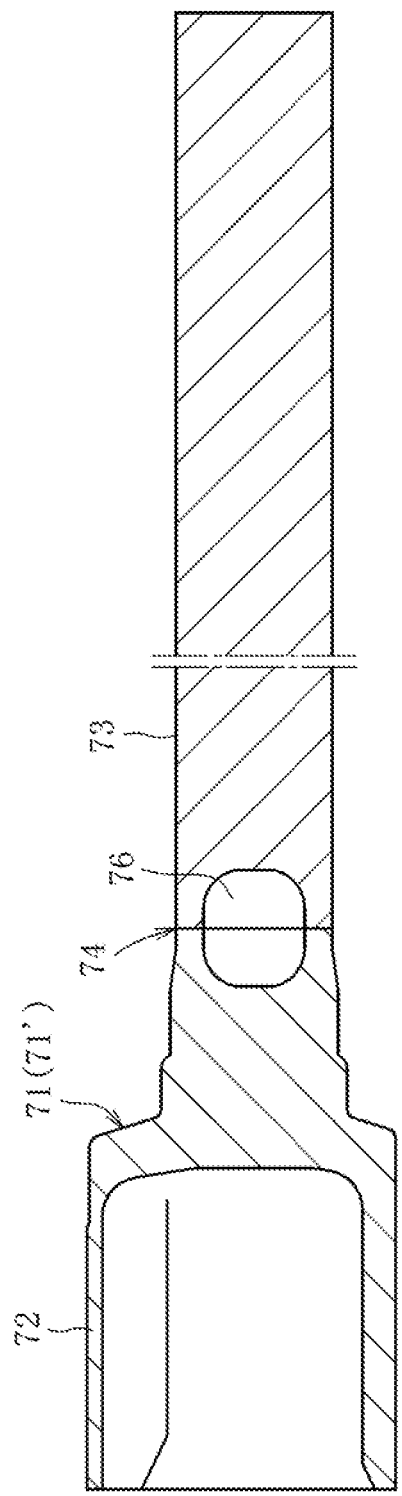
FIG. 25 is a vertical sectional view for illustrating an outer joint member according to a related art.

FIG. 22 is a partial vertical sectional view for illustrating the outer joint member $11_2$. As illustrated in FIG. 22, the outer joint member $11_2$ comprises a bottomed cylindrical cup section $12_2$ that is opened at one end and has inner peripheral surfaces $31_2$ and the track grooves $30_2$, on which the rollers 19 (see FIG. 21) are caused to roll, formed at three equiangular positions on an inner peripheral surface of the cup section $12_2$, and the long stem section 13 that extends from a bottom portion of the cup section $12_2$ in the axial direction and comprises the spline Sp serving as the torque transmitting coupling portion formed at the outer periphery of the end portion on the opposite side to the cup section $12_2$ side. The outer joint member $11_2$ is formed by welding the cup member $12_2a$ and the shaft member $13a$ to each other.

As illustrated in FIG. 22, the cup member $12_2a$ is an integrally-formed product having a cylindrical portion $12_2a1$ and a bottom portion $12_2a2$. The cylindrical portion $12_2a1$ has the track grooves $30_2$ and the inner peripheral surfaces $31_2$ formed at the inner periphery thereof. A projecting portion $12_2a3$ is formed at the bottom portion $12_2a2$ of the cup member $12_2a$. The boot mounting groove 32 is formed at an outer periphery of the cup member $12_2a$ on the opening side thereof. The bearing mounting surface 14 and the snap ring groove 15 are formed at the outer periphery of the shaft member $13a$ on the cup member $12_2a$ side, whereas the spline Sp is formed at the end portion on the opposite side to the cup member $12_2a$ side.

A joining end surface $50_2$ formed at the projecting portion $12_2a3$ of the bottom portion $12_2a2$ of the cup member $12_2a$ and the joining end surface 51 formed at the end portion of the shaft member $13a$ on the cup member $12_2a$ side are brought into abutment against each other, and are welded to each other by electron beam welding performed from the radially outer side. The welded portion 49 is formed of a bead, which is formed by a beam radiated from the radially outer side of the cup member $12_2a$. Similarly to the outer joint member of the first embodiment, the outer diameters B of the joining end surface $50_2$ and the joining end surface 51 are set to equal dimensions for each joint size. The welded portion 49 is formed on the joining end surface 51 located on the cup member $12_2a$ side with respect to the bearing mounting surface 14 of the shaft member $13a$, and hence the bearing mounting surface 14 and the like can be processed in advance so that post-processing after welding can be omitted. Further, due to the electron beam welding, burrs are not generated at the welded portion. Thus, post-processing for the welded portion can also be omitted, which can reduce the manufacturing cost.

The details of the outer joint member according to this embodiment are the same as the details of the outer joint member according to the first embodiment, and the manufacturing method according to the first to third embodiments as described above. Therefore, all of those details are applied in this embodiment to omit redundant description.

In the above-mentioned embodiments and the above-mentioned modifications, the case where the protruding surface is formed on the radially inner side with respect to the joining end surface of the cup member is exemplified. However, conversely, the protruding surface may be formed on the radially inner side with respect to the joining end surface of the shaft member. In this case, there are no problems as long as the ultrasonic flaw-detection inspection is performed from a surface side of the cup member.

In the above-mentioned embodiments and the above-mentioned modifications, the case to which electron beam welding is applied is described, but laser welding is also similarly applicable.

In the outer joint member according to the embodiments and the modifications described above, the cases where the present invention is applied to the double-offset type constant velocity universal joint as the plunging type constant velocity universal joint 10, and to the tripod type constant velocity universal joint as the plunging type constant velocity universal joint 10 are described. However, the present invention may be applied to an outer joint member of another plunging type constant velocity universal joint such as a cross-groove type constant velocity universal joint, and to an outer joint member of a fixed type constant velocity universal joint. Further, in the above, the present invention is applied to the outer joint member of the constant velocity universal joint, which is used to construct the drive shaft. However, the present invention may be applied to an outer joint member of a constant velocity universal joint, which is used to construct a propeller shaft.

The present invention is not limited to the above-mentioned embodiments and the above-mentioned modifications. As a matter of course, various modifications can be made thereto without departing from the gist of the present invention. The scope of the present invention is defined in Claims, and encompasses equivalents described in Claims and all changes within the scope of claims.

DESCRIPTION OF REFERENCE SIGNS 1 drive shaft
2 intermediate shaft
3 spline
4 boot
5 boot
6 support bearing
10 plunging type constant velocity universal joint
11 outer joint member
12 cup section
12a cup member
12a1 cylindrical portion
12a2 bottom portion
13 long shaft section
13a shaft member
14 bearing mounting surface
16 inner joint member
17 tripod member
19 torque transmitting element (roller)
20 fixed type constant velocity universal joint
21 outer joint member
22 inner joint member
23 torque transmitting element (ball)
24 cage
30 track groove
31 inner peripheral surface
40 track groove
41 torque transmitting element (ball)
42 cylindrical inner peripheral surface
49 welded portion
50 joining end surface
50a protruding surface
51 joining end surface
52 recessed portion
100 welding apparatus
101 electron gun
108 case
109 vacuum pump
111 sealed space
120 ultrasonic flaw detection-inspection apparatus
121 base
122 water bath
123 workpiece support
124 workpiece holding member
125 rotary drive device
135 pressing device
136 drive positioning device for probe
147 probe
B outer diameter
D inner diameter
E inner diameter
G transmission pulse
R reflected echo
O joint center
O1 curvature center
O2 curvature center
Sp spline

The invention claimed is:

1. A method of manufacturing an outer joint member of a constant velocity universal joint, which is constructed by forming, through use of separate members, a cup section having track grooves formed at an inner periphery of the cup section and engageable with torque transmitting elements, and a shaft section formed at a bottom portion of the cup section, and by welding a cup member forming the cup section and a shaft member forming the shaft section, the method comprising:
forming the cup member and the shaft member of medium carbon steel;
preparing, as the cup member, a cup member having a cylindrical portion and a bottom portion integrally formed by forging, and a joining end surface formed on an outer surface of the bottom portion in a machining step after the forging;
preparing, as the shaft member, a shaft member having a joining end surface to be joined to the bottom portion of the cup member, which is formed in a machining step;
bringing the joining end surface of the cup member and the joining end surface of the shaft member into abutment against each other;
welding the cup member and the shaft member by radiating a beam from an outer side of the cup member to an abutment portion between the cup member and the shaft member in a radial direction of the cup member, the joining end surface of the cup member having an outer diameter set to an equal dimension for each joint size,
the welding being performed under a state in which a protruding surface protruding to a radially inner side with respect to an inner diameter of another one of the joining end surface of the cup member and the joining end surface of the shaft member is formed on a radially inner side of any one of the joining end surface of the cup member and the joining end surface of the shaft member; and
performing, after the welding, ultrasonic flaw detection-inspection from any one of a surface side of the cup member and a surface side of the shaft member, which has the another one of the joining end surface of the cup member and the joining end surface of the shaft member.

2. The method of manufacturing an outer joint member of a constant velocity universal joint according to claim 1, wherein the ultrasonic flaw detection-inspection comprises performing flaw detection under a state in which the cup member and the shaft member after the welding are placed under water.

3. The method of manufacturing an outer joint member of a constant velocity universal joint according to claim 2, wherein the protruding surface is formed into the same shape for each joint size.

4. The method of manufacturing an outer joint member of a constant velocity universal joint according to claim 1, wherein the protruding surface is formed into the same shape for each joint size.

5. The method of manufacturing an outer joint member of a constant velocity universal joint according to claim 1,
wherein the protruding surface is formed on the joining end surface of the cup member, and
wherein the ultrasonic flaw detection-inspection comprises inputting an ultrasonic wave with an angle probe from the surface side of the shaft member.

6. The method of manufacturing an outer joint member of a constant velocity universal joint according to claim 1, wherein at least one of the cup member or the shaft member before the welding is prepared as an intermediate component without performing heat treatment.

7. The method of manufacturing an outer joint member of a constant velocity universal joint according to claim 1, wherein at least one of the cup member or the shaft member before the welding is prepared as a finished component subjected to heat treatment.

8. The method of manufacturing an outer joint member of a constant velocity universal joint according to claim 1, wherein the welding comprises electron beam welding.

9. The method of manufacturing an outer joint member of a constant velocity universal joint according to claim 1, wherein the welding comprises welding the cup member and the shaft member under a state in which the cup member and the shaft member are placed in a sealed space to keep a pressure equal to or less than an atmospheric pressure.

* * * * *